US006871015B2

(12) United States Patent
Gutierrez et al.

(10) Patent No.: US 6,871,015 B2
(45) Date of Patent: Mar. 22, 2005

(54) COMPARTMENTALIZED DISPENSING DEVICE AND METHOD FOR DISPENSING A FLOWABLE PRODUCT THEREFROM

(75) Inventors: J. Antonio Gutierrez, Kent, CT (US); Balakrishna Reddy, Ridgefield, CT (US); Hua Zhang, New Milford, CT (US)

(73) Assignee: Nestec S.A., Vevey (CH)

( * ) Notice: Subject to any disclaimer, the term of this patent is extended or adjusted under 35 U.S.C. 154(b) by 464 days.

(21) Appl. No.: 10/032,170

(22) Filed: Dec. 21, 2001

(65) Prior Publication Data

US 2003/0116584 A1 Jun. 26, 2003

(51) Int. Cl.[7] .................................................. A61F 7/00
(52) U.S. Cl. ..................... 392/470; 222/146.1; 222/325
(58) Field of Search ................................ 392/470, 471, 392/474; 222/146.1, 375, 94, 95, 105

(56) References Cited

U.S. PATENT DOCUMENTS

| | | | | |
|---|---|---|---|---|
| 3,173,579 A | | 3/1965 | Curie et al. | 222/105 |
| 3,212,681 A | | 10/1965 | Weikert | 222/183 |
| 3,297,206 A | | 1/1967 | Scholle | 222/105 |
| 3,435,990 A | | 4/1969 | Pike, Jr. | 222/1 |
| 3,520,451 A | | 7/1970 | Ashizawa | 222/148 |
| 4,094,446 A | | 6/1978 | Brutsman | 222/146 HE |
| 4,141,474 A | | 2/1979 | Nilson | 222/493 |
| 4,544,085 A | | 10/1985 | Frazer | 222/146.4 |
| 4,651,898 A | | 3/1987 | Bell | 222/129 |
| 4,717,047 A | | 1/1988 | van Overbruggen et al. | 222/207 |
| 4,796,788 A | | 1/1989 | Bond | 222/94 |
| 4,913,713 A | | 4/1990 | Bender et al. | 62/3.61 |
| 4,941,597 A | | 7/1990 | Lopez et al. | 222/146.5 |
| 5,000,351 A | | 3/1991 | Rudick | 222/105 |
| 5,040,700 A | | 8/1991 | Compton | 222/146.5 |
| 5,102,015 A | | 4/1992 | Barnard et al. | 222/135 |
| 5,114,045 A | | 5/1992 | Herpe | 222/105 |
| 5,142,610 A | | 8/1992 | Augustine et al. | 392/442 |
| 5,249,706 A | | 10/1993 | Szabo | 222/20 |
| 5,301,601 A | | 4/1994 | Cretors | 99/323.5 |
| 5,349,825 A | | 9/1994 | Duke et al. | 62/69 |
| 5,353,963 A | | 10/1994 | Gorski et al. | 222/129.1 |
| 5,366,308 A | | 11/1994 | Crispino | 401/1 |
| 5,634,343 A | * | 6/1997 | Baker, III | 62/3.64 |
| 5,803,317 A | | 9/1998 | Wheeler | 222/214 |
| 5,938,078 A | | 8/1999 | Dorsey et al. | 222/105 |
| 6,003,733 A | | 12/1999 | Wheeler | 222/146.5 |
| 6,016,935 A | | 1/2000 | Huegerich et al. | 222/146.1 |
| 6,056,157 A | | 5/2000 | Gehl et al. | 222/94 |
| 6,089,406 A | | 7/2000 | Feldner | 222/103 |
| 6,095,372 A | | 8/2000 | Dorsey et al. | 222/105 |
| 6,223,944 B1 | | 5/2001 | Gehl et al. | 222/94 |
| 6,378,730 B1 | | 4/2002 | Reddy et al. | 222/83 |
| 6,419,121 B1 | | 7/2002 | Gutierrez et al. | 222/146.5 |
| 6,488,179 B1 | | 12/2002 | Vujicic et al. | 222/132 |
| 2002/0139815 A1 | | 10/2002 | Tansley et al. | 222/105 |

* cited by examiner

*Primary Examiner*—Thor Campbell
(74) *Attorney, Agent, or Firm*—Winston & Strawn LLP

(57) ABSTRACT

The invention relates to a method for rapidly, efficiently heating and dispensing a flowable food product, using a device preferably of limited footprint whereby removable cassettes are provided for receiving a food-containing package. The cassettes at least include a direct conduction surface and an insulating coverage that substantially reduces radiant heat loss outside the cassettes. Preferably, there is provided peristaltic pumps, each one being adapted to engage a discharge tube of the food pouch wherein the pumps have their rotor plane oriented in alignment or parallel to the axial plane of the cassettes. Cassettes are heated by low power density generating heating members, such as a thin film heater or equivalent.

34 Claims, 17 Drawing Sheets

COMPARTMENTALIZED DISPENSING DEVICE AND METHOD FOR DISPENSING A FLOWABLE PRODUCT THEREFROM

FIELD OF THE INVENTION

The invention relates to a compartmentalized dispensing device and method for dispensing flowable materials from packages such as pouches and the like and, more particularly, to a device and method for more accurately, uniformly and rapidly heating a food product and/or maintaining cool a food product and for dispensing the food product at a desired controlled temperature from the package.

BACKGROUND OF THE INVENTION

Heated or refrigerated dispensers for delivering liquid or semi-liquid food products are commonly used in foodservice restaurants, catering, convenience stores and other commercial or public food establishments. The known dispensers are usually adapted for receiving food bags in a housing and for delivering the food by using pumps and/or gravity forces to a dispensing area.

Food products, such as cheese sauces and the like, usually requires to be served at warm temperature to adapt to culinary habits and/or to improve the digestion of fat. Other food products are adapted to be stored and dispensed cold such as salsa, ketchup or condiment sauces. Other foods are adapted to be dispensed at refrigerated temperatures such as UHT cream, yogurt, acidified milk based food or pudding. These food products may be easily subjected to bacterial spoilage when opened, whereby heating or cooling permits to keep the food in safer bacteriological conditions. The products usually need to be stored in aseptically hermetic flexible packages such as pouches, which are opened at the time the product is dispensed and therefore become sensitive to airborne pathogens. The problem is that the pouches are usually of relatively large size, in general of several kilograms, thus requiring a relatively long time before obtaining a controlled hot/cool temperature acceptable for serving.

One disadvantage of having a long heat-up/cooling-down time is that a fully warm/cool food package may not be rapidly available when the demand for food exceeds the warming/cooling operation time for the new package. Another disadvantage is when the package is opened before the product reaches a sufficiently safe temperature level, i.e., about 60° C. in the case of hot product or below 4–6° C. for refrigerated products, the risk of bacterial contamination or spoilage may seriously increase.

For instance, the American NSF standards require that potential hazardous food products having a pH level of 4.6 or less to be rethermalized; i.e., heated from refrigerated or ambient state to an elevated temperature of not less than 140° F., must be capable of heating the food product to that temperature within four hours. For example, by using existing commercial equipment, the average heat-up time for large size pouches is of more than 3 hours, most often more than 5 hours and sometimes more than 10 hours, before the temperature in the center part of the pouch can be raised from ambient to an acceptably warm temperature of 60° C.

In order to meet with these regulations, prior solutions consisted in pre-warming the bag in a hot water bath or in microwave oven, then transferring the preheated bag to the dispensing unit where the bag remains temperature controlled. However, this is not always satisfactory as it requires that an additional piece of equipment be available for heating. A water bath is usually cumbersome and requires a long time to warm up. Microwave heating also suffers from non-homogeneous heating problems with formation of cold and hot spots in the food. It also requires manipulation and surveillance by the foodservice operators to transfer the food pouch from the microwave unit to the holding unit. Handling of the bags when hot is not convenient and may cause burns for the operator due to contact with heated parts of the dispensing unit.

Similarly, there are food products that are preferably served slightly below ambient, such as cold sauce, salsa, ketchup, condiments and the like, so that the shelf life of the product in the dispensing unit can be prolonged significantly. Especially in hot seasons and non air-conditioned rooms, it is advisable to keep these type products at a temperature below 18° C., and preferably below 15° C. or lower. The known condiment or ketchup dispensing units usually have no cooling systems. The dispensing units for these products are usually kept separate from the dispensing units for hot products such as the cheese sauce dispensers. This is not convenient as this requires more room for storing those separate units.

Furthermore, the prior art does not disclose a dispensing device that is flexible enough in its design to be capable of providing either heat or cooling upon demand depending upon the needs while involving as little handling for the operator as possible.

U.S. Pat. No. 5,803,317 to Wheeler relates to a heated dispensing apparatus for dispensing products at elevated temperature which allows packaging of the product in a container, such as a flexible bag, with a discharge tube extending therefrom. The dispenser includes a receptacle with an outlet opening in the lower portion thereof and a pump adjacent to the outlet opening. A heater is provided for heating the food bag in a large heat-conductive receptacle and the discharge tube passing through the pump and maintaining both the bag and the tube at a desired elevated temperature. The receptacle is permanently mounted on the dispenser frame and accommodates the reception of a bulky flexible package with a fitment protruding on one side of the package. Therefore, loading of the package in the dispenser requires opening of the dispensing unit thus creating thermal loss and risks of burn. Furthermore, due to the position of the bag in the receptacle and the open configuration of the receptacle, the thermal transfer from the receptacle to the bag remains relatively poor, thereby leading to excessive heat-up time when packages are loaded for rethermalization. Furthermore, the heat loss is significant as the receptacle itself, especially its non-contacting parts, may form an important heat sink for the package. In addition, this dispensing system cannot be used for cooling and dispensing foodstuff.

U.S. Pat. No. 6,003,733 relates to an apparatus for the dispensing of heated viscous food product using convection means. The problem is that this heating mode requires more room for the air to properly circulate around the bags thereby rendering the apparatus more cumbersome. The heat also dissipates rapidly when the operator opens the heated cabinet for replacing a bag or maintenance therefore creating significant temperature drops and important heat losses. Furthermore, this dispensing system also cannot be used for cooling and dispensing foodstuff.

U.S. Pat. No. 6,016,935 relates to a viscous food dispensing and heating/cooling assembly which is adapted to receive large food reservoirs of the "bag-in-box" type in a manner similar to the previous patent references; the improvement consisting in a specific air flow circulation to heat both the reservoir and the discharge tube. This device has the same shortcomings as the previous patents.

U.S. Pat. Nos. 6,056,157 and 6,223,944 to Gehl relate to a dispensing device for a flowable substance comprising a housing comprising walls to define a compartment, a heating unit for maintaining the compartment at a predetermined temperature, a valve for selectively controlling flow of the material from the package. This device includes a dispensing portion and an actuating portion wherein the dispensing portion, which includes a valve body and a valve outlet, is entirely within the compartment and heated by the heating unit. This configuration requires the operator's direct handling of the package and manual connection of the package to the dispensing portion which both receive heat from the heating unit. Furthermore, a significant heat loss occurs when the operator opens the device for replacing the bag.

German company Herman Roelofsen GmbH manufactures food dispensing units comprising a relatively wide box-shaped aluminum container adapted to receive a flexible food bag. The bag is loosely housed within the container and a bar inserted in two slots of the container hangs up the bag to avoid collapsing of the bag within the container. The container fits within a heating metal compartment of the unit which is heated by flexible heating devices. Due to heat loss in the transitions and air gaps from the heaters to the food, the dispensing unit has poor heating performance on large size bags with an heat-up time of more than 10 hours from ambient state for cheese sauce bags. Therefore, microwave preheating of the bag is required before the bag can be installed in the dispensing unit. Furthermore, such dispensing system cannot be used for dispensing refrigerated foodstuff.

Thus, there is a need in the art for improved dispensing systems, and this is now satisfied by the present invention.

SUMMARY OF THE INVENTION

The invention provides a dispensing device that confers an improved heating or cooling output over the existing devices of the prior art, increases the amount of hot or cooled product available for dispensing, in particular, by reducing the heat-up/cooling down time significantly and is easy to hold the product at the desired controlled temperature while being less energy consuming than existing equipment.

The invention improves the convenient and safe handling of food containers from an operator's point of view while minimizing the operator's manipulation and eliminating hazards such as risks of burns with the container and/or hot parts of the device.

The present dispensing device has a reduced footprint without detriment to the dispensing capacity, and ensures a faster and more uniform heating or cooling of on-demand delivered food.

The invention also provides a dispensing device whereby uniform and optimal heating is promoted within the container with no significant heat gradient and overheating, therefore avoiding quality and safety issues as well as increasing the shelf life of the products that are dispensed by the unit.

The invention also ensures more continuity in delivering food product at a desirable controlled temperature; i.e., hot and/or cool temperatures to below ambient, and convenience for the foodservice operator. It thus provides the opportunity to include in the same unit products that require to be served hot or warmed such as cheese sauce and also products that require to be served at ambient temperature or slightly lower such as ketchup, sauce or salsa without the second ones being incidentally warmed by the first ones. Therefore, a better preservation and extended shelf life of cold served food products are obtained in the dispensing device after the first opening of package food products therein.

A first aspect of the invention is based on the principle of a dispensing device comprising a housing adapted to accommodate in a removable manner at least one substantially closed cassette having built-in temperature exchange means that provides direct heat or cooling along at least one heated or cooled surface to a food-containing package and insulating means for preventing significant radiant heat or frigorific loss to outside the boundaries of the cassettes.

In a preferred aspect, the cassette has an extensive interior oriented along an axial plane and are narrowly shaped in a transversal direction to this axial plane with at least one extensive heating or cooling surface of the interior directly heating or cooling the package. The cassette is substantially closed around the package except a passage for the delivery of the food. For instance, the passage may be sufficient for a discharge tube and fitment assembly to pass through the passage but with the passage in sufficiently close fitting with the tube and fitment assembly to avoid significant thermal losses.

Even preferably, the interior of the cassette has heating or cooling means directly heating or cooling at least two extensive conduction heating or cooling surfaces extending substantially parallel to the axial plane and transversal sides demarcating a narrow spacing for intimate heating contact with the package and heating in a direction normal to the two extensive conduction heating surfaces. Therefore, the food product is more rapidly and efficiently heated since the food product spreads over an overall large heating surface and receives heat from two opposite sides orthogonally to the smallest dimension of the interior of the cassette. Even preferably, the cassette has built-in heating means providing direct heat to at least five sides, even more preferably the six sides of the cassette, that form conduction heating surfaces in contact with the package. In order to further obtain a significant reduction of the heat-up time while more uniformly controlling the food temperature, the spacing or smallest transversal dimension is preferably less than 2 inches, even preferably less than 1 and ¾ inches.

Preferably, the at least one heating surface receives heat from a heater under the form of a heat resistive substrate that uses energy converted into heat based on the resistivity of the material that electricity is flowing through. More preferably, the heater is chosen so to deliver an average power density of at least 0.3 Watts per square inch. Even preferably, the heater is capable of delivering a varying power density as a function of the location along the heating surfaces so as to provide a more uniform temperature throughout the product. For that, it is preferred to have a power density that varies from 0.3 W/sq.in to 0.8 W/sq.in, preferably from 0.45 W/sq.in to 0.65 W/sq.in. More preferably, the areas of higher power density, i.e., 0.6 to 0.8 W/sq.in, preferably of about 0.65 W/sq.in, are located in the bottom side of the cassette and near the passage for the discharge tube and fitment assembly. The areas of lower power density, i.e., 0.3 W/sq.in. to 0.55 W/sq.in., preferably about 0.45 W/sq.in., are located in the substantially planar areas of the heating surfaces so as to heat the body of the pouch. This results in a more uniform heating than with a single power density.

The heater preferably comprise a flexible heater that is capable of being folded in order to provide heat along at least two distinct planes, preferably along at least five distinct planes, even preferably along six distinct planes. Preferably, the flexible heater is at least one thin film heaters per cassette. Thin films of large areas used in the cassette allows substantial power to be delivered but at a low density average power density therefore providing a very efficient heating at low cost and with lower risks of overheating.

In another important aspect of the invention, in order to receive appropriate electrical power for its built-in heating or cooling means while avoiding time consuming manipulations, the cassette includes a self-aligning plug-in electrical connection means and the housing comprises complementary electrical receiving means adapted to complementary fit the electrical plug-in connection means of the cassette. The electrical plug-in connection means of the cassette is arranged to plug in to the electrical receiving means in the housing as directly resulting from the completion of the loading of the cassette within the housing. Therefore, the loading of the cassettes in the device is quick and convenient and does not require difficult and time consuming manipulation or handling from the operator. More particularly, electrical plugging of the cassette is carried out as resulting from the complete insertion of the cassette within the housing, preferably after sliding engagement of the cassette within the housing. For that, guiding means may be provided in the housing to guide the cassette in engagement within the housing until the cassette is inserted in the correct plug-in position. The cassette may preferably comprise complementary fitting means that cooperate in engagement with the guide means of the housing so as to aid the proper physical and electrical insertion of the cassette within the housing.

In another important aspect of the invention, an accurate and safe temperature control in the cassette is carried out by providing in the cassette at least one built-in product sensing means adapted to sense the package surface temperature and at least one built-in heater sensing means adapted to sense the heater surface in the cassette, both product and heater sensing means are adapted to provide temperature feedback to a controller of the device in accordance with a predetermined logic routine. Preferably, in order to obtain a more rapid heat-up of the food temperature while ensuring the food product does not experience overburning, the heating of the package is accurately controlled according to at least two separate heating modes; a first boost mode whereby heating in the cassette by the heater is carried out to a predetermined elevated temperature range of the heater and a second monitoring or maintenance mode whereby the heating of the cassette by the heater is carried out at a predetermined heater temperature range lower than the temperature range of the boost mode.

More preferably, for activating the boost mode, the temperature of the product must initially be sensed by the product sensing means below a product temperature threshold (lower than the product monitoring set point), e.g., 120° F., which allows to set a boost elevated set point for the heater temperature, e.g., 175° F.+/−tolerance value(s), until the product sensor reaches a product monitoring set point, e.g., 150° F.+/−tolerance value(s). Once the product monitoring set point is reached, the product sensor takes over the control and the heater sensor changes over to the monitoring mode and controls the heater surface not to exceed a lower set point of the heater temperature, e.g., 165° F. If the initial product temperature sensed by the product sensor is higher than the product temperature threshold, the boost cycle may be skipped and the monitoring mode may take place immediately after insertion of the cassette so that the product temperature is monitored at the predetermined product monitoring set point, e.g., 150° F.+/−tolerance value(s).

Such an exemplary control logic configuration promotes a precise and reliable temperature control, a temperature maintenance at optimal levels to achieve best quality through the life of the product and, a rapid rising of the product temperature in all conditions, whereas the product may be initially cold or already warm, while it also anticipates on the heater inertia to insure the product cannot be overburnt.

The boost and monitoring modes may preferably be carried out by a single resistive heating circuit of the cassette and can be controlled by the use of an electronic proportional controller that regulates the electric power based on the signal that is proportional to the differential of sensor temperature from the established set point. In an alternative, the control is obtain by a pulsing controller that pulses to a full power on/off alternatively.

In another inventive aspect, in order to assist dispensing of relatively viscous foodstuff, there is provided at least one volumetric displacement pump such as a peristaltic pump, that is independent of the cassette and is adapted to engage a discharge tube of the food package. The discharge tube is preferably heated directly in a manner separate from the cassette. Thus, the temperature of the product in the tube can be more accurately controlled and less the energy is used for maintaining the tube at the required hot temperature in the tube. The discharge tube can be controlled at a predetermined hot temperature by suitable heating means associated to a temperature sensing means that provides temperature feedback to the controller. The heating means may be coupled to a part of the pump in contact with the tube or may, alternatively, be directly coupled to the discharge tube.

In another advantageous aspect of the invention, the volumetric displacement pump is a peristaltic pump with its rotor plane oriented in alignment or parallel to the axial plane of the at least one cassette or, similarly, in alignment or parallel to the axial plane of the cassette location in the dispensing device. Therefore, the orientation of the pump participates to the reduction of the footprint of the device while it also renders the installation of the package easier and quicker.

In a preferred aspect, the device comprises a series of cassettes as defined above that are interchangeable in the housing. A plurality of cassettes enables to ensure a continuity in the supply in hot and/or cool food product. Each cassette is preferably oriented with its axial plane substantially vertical within the housing to promote gravity flow.

In another aspect, the invention relates to a heating or cooling cassette adapted to fit in a dispensing device as aforementioned.

The invention also relates to a dispensing device for dispensing flowable food product comprising:

- a housing;
- at least a pair of removable cassettes within the housing; each cassette having an axial plane and being adapted for receiving a package containing flowable food substantially laying along the axial plane;
- wherein each cassette has a closed interior for receiving the package and comprises at least one extensive direct conduction heating surface extending substantially parallel the axial plane of the cassette.

Preferably, the interior of each cassette has at least two extensive direct conduction heating surfaces extending along the axial plane and transversal sides demarcating a narrow spacing wherein the spacing is below 2 inches, preferably below one and ¾ inches. A limited spacing as defined allows the food product to intimately spread along the heating surfaces regardless of the package capacity while eliminating the areas of higher thermal inertia in the food product. Such spacing promotes lowering of the heating rate of the package and requires less energy for constantly maintaining the package at an elevated temperature. Therefore, it also contributes to more uniformly and accurately control the temperature of the food product with reduction of heat gradients. Consequently, it is made possible to eliminate the hot spots which normally create local browning of the food, thereby affecting the quality and shelf life of the food product. The temperature of the food product can also be more easily maintained substantially uniform and constant over time at a required temperature level, thereby similarly ensuring a longer shelf life. Although not expressly limited to large capacity packages, the invention promotes a more efficient, accurate and rapid heating of the food product; i.e., in less than 2 and ½ hours from ambient, preferably 2 hours or less, for packages containing more than 2.5 Kg, e.g. for 3.0 Kg of food product.

In a preferred mode, at least two interchangeable cassettes are provided within the housing to offer the possibility to have a first dispensing cassette and a second preheating cassette; the dispensing cassette being removable to be replaced by the preheated cassette at any desired time after the food in the preheated cassette has reached a monitoring temperature within the housing.

Preferably, the first cassette is positioned in the housing in a position adapted to a dispensing mode; e.g., whereby the outlet opening of the cassette may preferably substantially be aligned with valve means. Preferably, the valve means is a volumetric displacement pump such as a peristaltic pump. Still in a preferred mode, the first and second cassettes are configured in parallel in the housing to permit one cassette to be replaced by the other more easily. The cassettes may preferably be removable from the housing by sliding motion of the cassette(s) in a primary direction after opening of the housing.

It is meant that the same modularity approach can be applied for cooling of the pouch; i.e., using dispensing cooled cassette(s) which can be exchanged one by the other to ensure a continuity in the supply of cooled product and, therefore, provide more convenience to the foodservice operator. It is also possible to have both at least one heating cassette and at least one cooling cassettes in the housing to both dispense hot food product and cool product separately via separate volumetric displacement means. Cooling of the food products is primarily sought to ensure an extended shelf life and keep longer freshness of the product.

The modularity approach with a plurality of cassettes having built-in heating or cooling means with further built-in temperature sensing means also offers the opportunity to have a plurality of cassettes that can be controlled independently from a central controller located in the dispensing unit. Hence, cassettes can be independently monitored at different temperatures so to deliver in the same dispensing unit products of the same or different types at different temperatures.

In another aspect, the invention relates to a heating device of reduced foot print adapted for providing a high capacity in heated flowable food whereby removable cassettes are provided for receiving a package containing food; the cassettes comprising an interior with internal direct conduction heating surfaces wherein the interior has a width of less than 2 inches and insulating external means are provided to reduce radiant loss and facilitate handling and loading of the cassette out and in the heating device.

Another aspect of the invention relates to a dispensing device of reduced foot print adapted for providing a high throughput of heated or cooled flowable food whereby at least a pair of removable cassettes is provided for receiving a food-containing package; the cassettes comprising built-in electrical heating or cooling means wherein it comprises at least one peristaltic pumping means for dispensing the food out of the dispensing device having its rotor plane oriented in alignment or parallel to the axial plane of at least one cassette. In particular, the device is capable of having at least four locations for the cassettes while respecting an external width of less than 10 inches, preferably about 9 inches.

Another aspect of the invention relates to a dispensing device for dispensing flowable food product comprising a housing at least a removable cassette within the housing adapted for receiving a package containing flowable food wherein the cassette has a closed interior for receiving the package and comprises built-in heating or cooling means providing direct heat or cooling to at least one extensive conduction heating surface extending substantially parallel the axial plane of the cassette; and built-in sensing means and further a centralized control means including a controller and wherein the sensing means comprise at least one temperature product sensor and at least one heater sensor both providing temperature signals to the centralized controller to precisely control temperature inside the cassette. Preferably, the dispensing device has a plurality of cassette locations adapted to receive a plurality of cassettes having built-in heating or cooling means and built-in sensing means allowing independent monitoring of the product temperature inside each cassette.

In an aspect the invention also relates to a method for rapidly and uniformly heating a food package in a dispensing unit wherein it comprises the use of at least one removable cassette provided for individually receiving a food-containing package wherein the cassette is effective to heat a food package while delivering an average power density of at least 0.3 W/sq. in. but less than 1 W/sq.in. by direct conduction effect with heating elements directing heat at least in a direction transversal to the axial plane of the cassette through the width of the cassette.

BRIEF DESCRIPTION OF THE DRAWINGS

The details of the preferred embodiments of the invention are illustrated in the appended drawings figures, wherein.

DETAILED DESCRIPTION OF THE PREFERRED EMBODIMENTS

Figure 1:
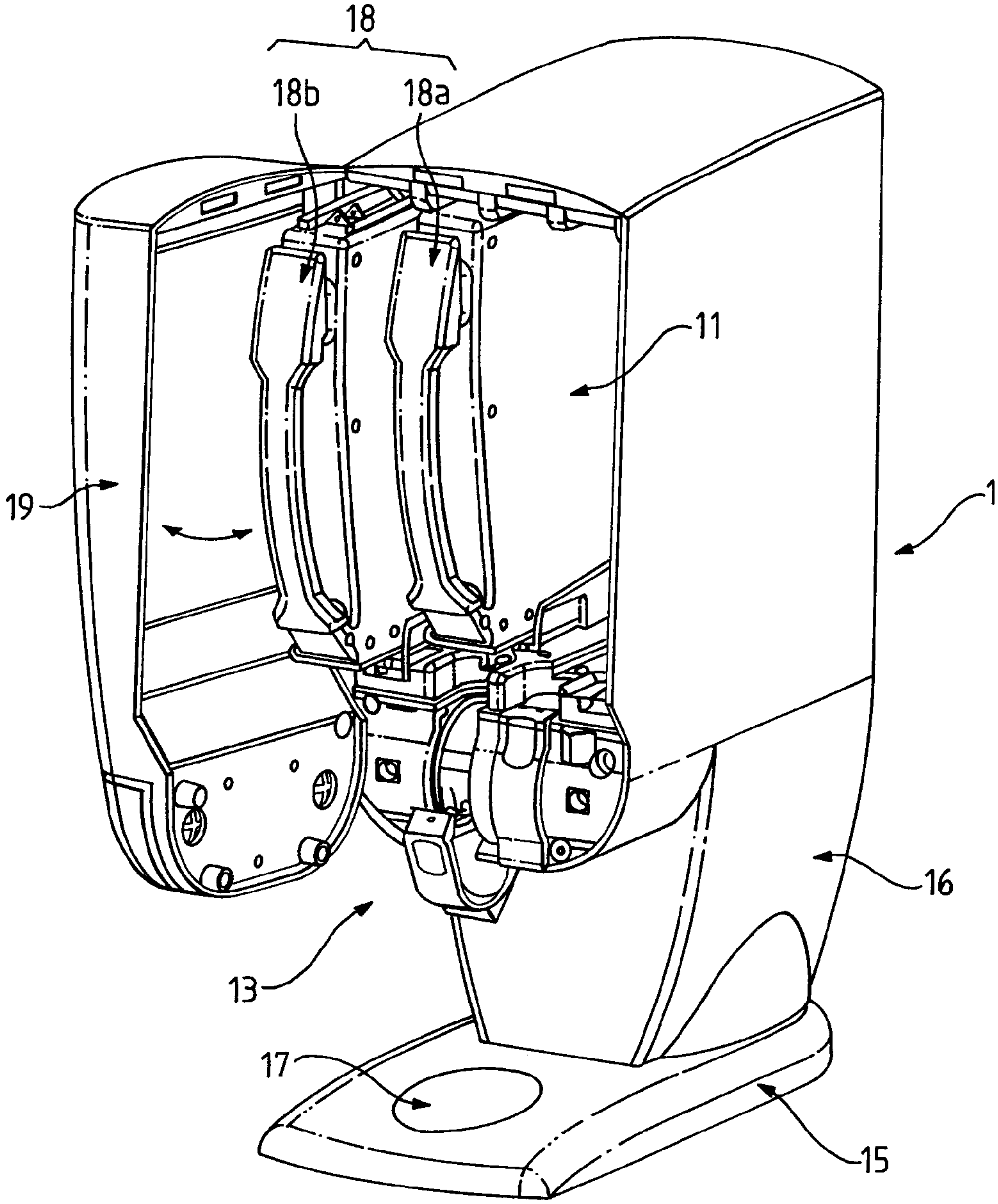
FIG. 1 relates to a perspective view of the heated dispensing device of the present invention with its front panel being opened.
Figure 2:
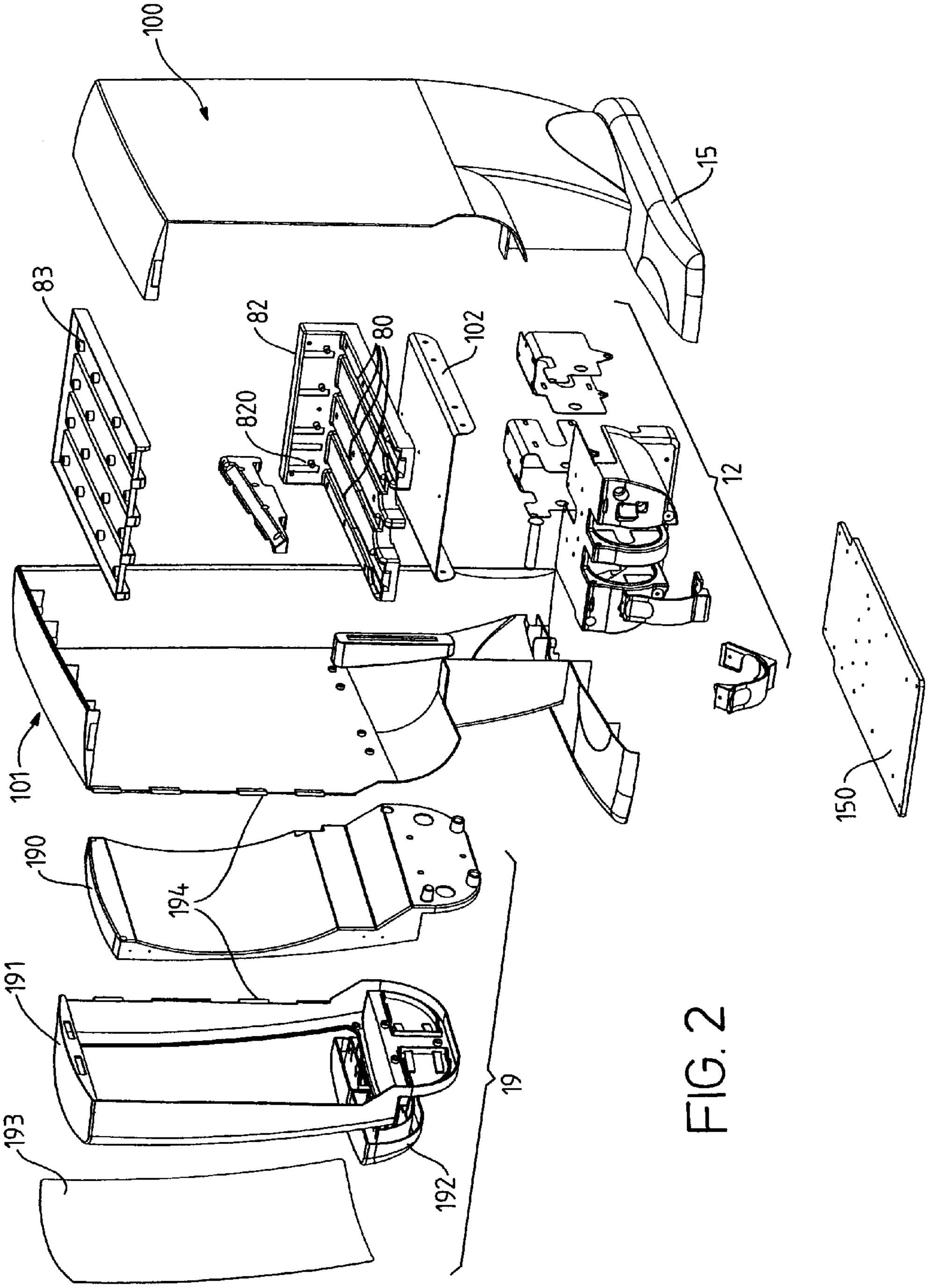
FIG. 2 is an exploded perspective view of the dispensing device of FIG. 1.
Figure 3:
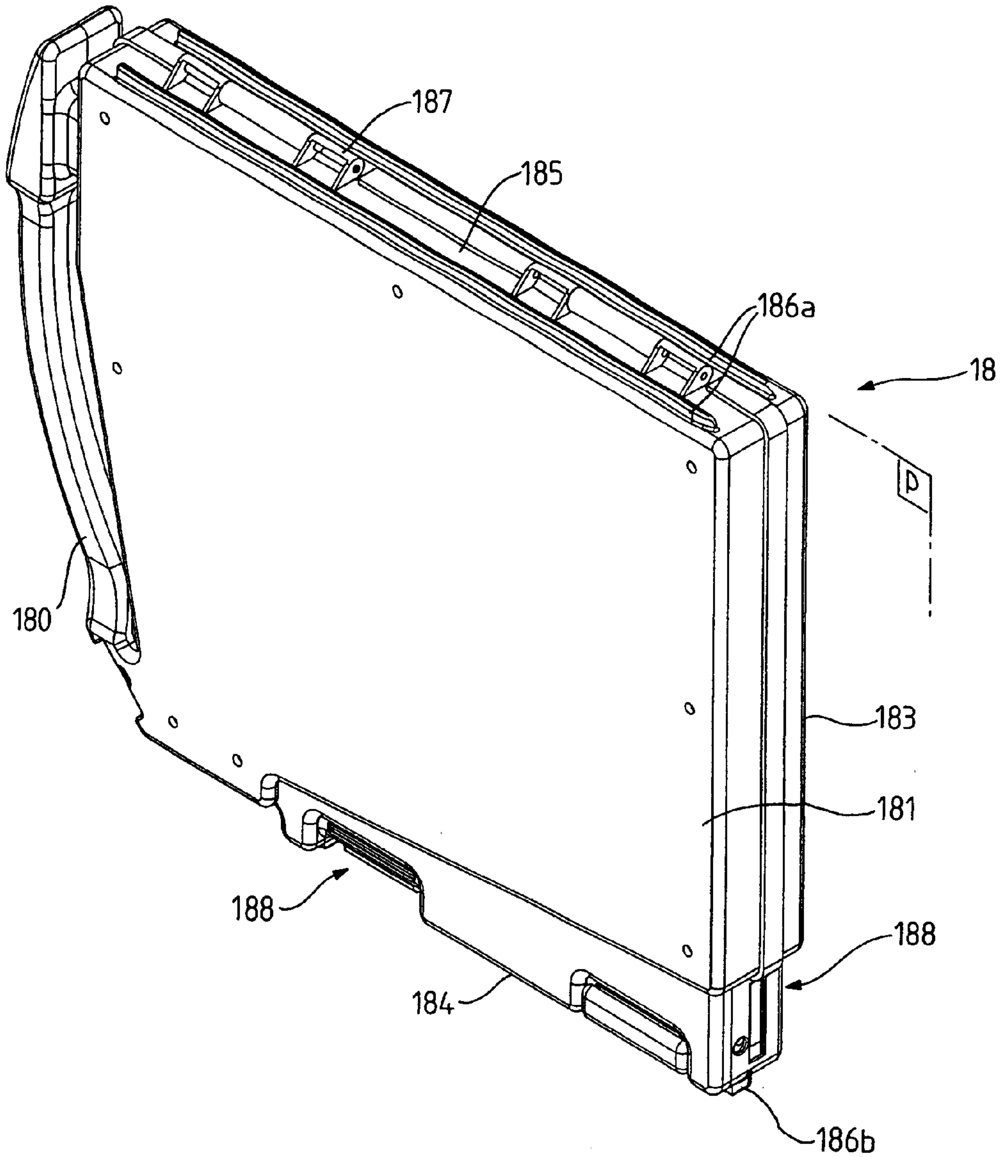
FIG. 3 is a perspective view of a cassette according to a preferred embodiment of the invention.
Figure 6:
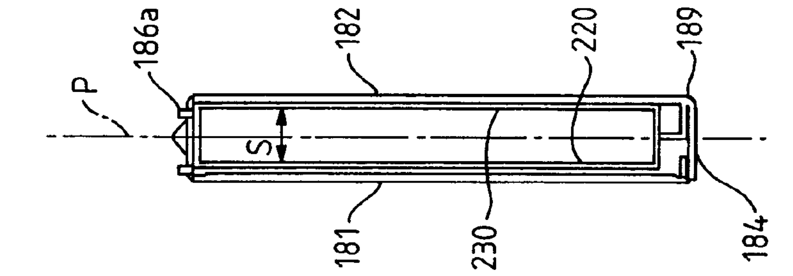
FIG. 6 is a cross-section view of the cassette of FIG. 4 along B—B of FIG. 4.
Figure 5:
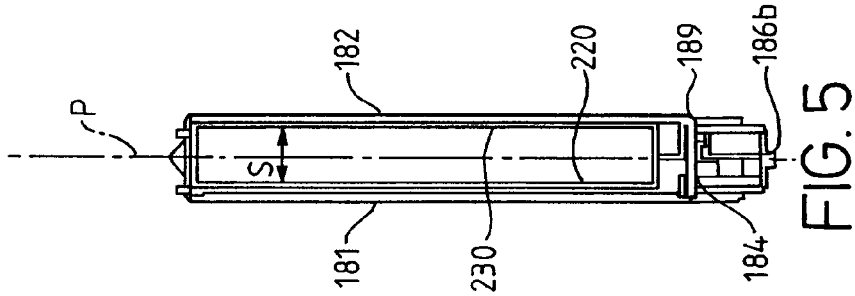
FIG. 5 is a cross-section view of the cassette of FIG. 4 along A—A of FIG. 4.
Figure 4:
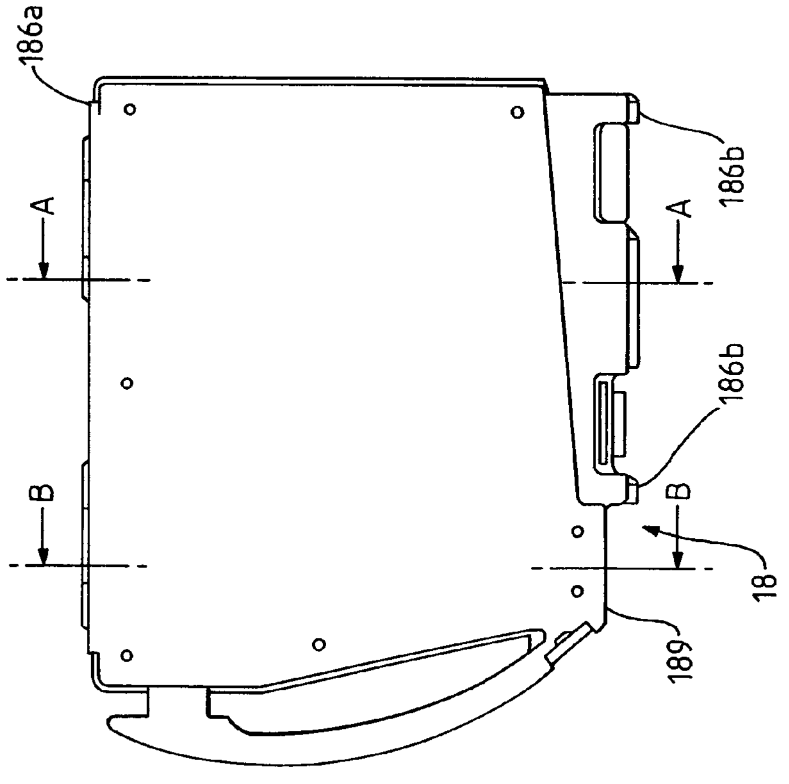
FIG. 4 is a side view of the cassette of FIG. 3.

Referring initially to FIGS. 1 and 2, the dispenser is shown generally by the character numeral 1 and includes a main housing 10 demarcating an interior cavity 11, a lower block 12 comprising volumetric displacement means 13, 14 for dispensing accurately food portions, a pedestal 15 and a stanchion portion 16 extending vertically from near the rear of the pedestal so as to leave a front dispensing area 17 allowing a recipient to be positioned to receive the food product from the device. In FIGS. 1 and 2, the front panel assembly 19 is opened with respect to the housing along side hinges 194 to show the interior configuration within the housing 10. The front panel assembly 19 may include an insulating block 190, a frame block 191, a switch board 192 and an outer decorative panel 193. A fluorescent back light system with one or several fluorescent bulbs may be further provided that automatically switches on by means of suitable relays when the front panel is opened.

In a preferred aspect of the invention, the housing is adapted to accommodate a plurality of individual narrowly profiled cassettes 18 which can be vertically arranged in parallel within the housing. A vertical arrangement of the cassette along their primary axial plane is preferred to promote gravity flow of the product contained in the package inside the cassette. The cassettes are insertable in the interior cavity 11 in sliding engagement along guiding means, in particular, sets of slots including lower slots 80 and upper slots 81 provided respectively in a lower base support 82 and in an upper base support 83. The lower and upper base supports may be fixed to the housing between two half-frames 100, 101 that longitudinally connect together by means of connection means such a rigid metal connecting plate 102 and other elements such as screws and the like, as illustrated in FIG. 2. In order to ensure rigidity and stability to the pedestal, a lower plate 150 may be further provided that is screwed to the bottom of the half-frames. The lower pumping block 12 is also partially inserted between the two half-frames 100, 101 and fixed by any one of a variety of connection means (not shown). Its detailed structure will be further described later in the present description.

FIG. 1 shows the dispensing system in an open configuration with a cassette 18*a* partially inserted in the housing along a first set of slots defining a first cassette location and a second cassette 18*b* fully inserted along a second set of slots defining a second cassette location. The housing may have as many cassette locations as sets of slots provided in the housing, as for instance, four cassette locations corresponding to fours sets of slots arranged in parallel, as illustrated in the preferred drawings. The number of cassette locations is not limited and depends upon the required capacity of the device and/or the types of food to be dispensed. However, the number of cassette locations of the device should preferably be a multiple of 2 as it is envisioned preferably that the device comprises cassettes which may be either in a dispensing mode or in a preheating mode within the housing. More specifically, as shown in FIGS. 1 and 2, the housing is configured to have operational dispensing locations, e.g., the two central locations in the preferred embodiment, and preheating locations, e.g., the two end locations in the preferred embodiment. The locations depend on how the pumping assemblies are configured underneath. A dispensing location is preferably a place dedicated to a cassette within the housing where the cassette is substantially aligned to a pumping assembly so as to enable a substantially straight connection of the dispensing means to the pumping assembly underneath. Similarly, a preheating location does not necessarily require a pumping assembly underneath although it is also possible to envisage a pumping assembly. The benefit of the preheating mode is mainly to have, at disposal, a place for preheating the cassette, eventually holding the cassette hot at the desired temperature controlled set point, until there is a need for dispensing product at the controlled temperature from the cassette.

FIGS. 3 to 7 show a preferred embodiment of the cassette of the invention. The cassette is constructed such that it is structurally rigid and maintain its shape when a food package is loaded in it. The cassette defines a substantially closed interior 19 of sufficient capacity for receiving a food package, usually a flexible pouch, that is substantially sized and dimensioned to intimately conform to the interior 19. The cassette may preferably have a substantially rectangular external shape of narrow profile to occupy as less room in the transversal dimension as possible in the housing. The cassette comprises a front side 180, extensive lateral sides 181, 182, a rear side 183, a lower side 184 and upper side 185. The front side 180 of the cassette may preferably comprise a handle made of heat insulated material such as of thick plastic to facilitate handling of the cassette, prehension and access to the cassette when the cassette is inserted in the dispensing unit and insertion of the cassette in the dispensing unit. The lower side 184 and upper side 185 include sliding means that help to guide the cassette in the slots provided in the housing. Such sliding means may, for instance, be formed as rails, either discrete or continuous 186*a*, 186*b* protruding respectively outward the upper side and lower side of the cassette. In the bottom side 184 of the cassette is provided an outlet 189 forming a passage for the tube and fitment assembly of the package.

In the bottom of rear side 183 of the cassette is located a plug-in electrical connection 188 which is adapted to fit a complementary electrical receiving connection 820 located in the rear wall of the interior cavity of the housing (connection 820 is apparent in FIG. 2). The electrical connection 188 bears the power and control connections necessary for the cassette to provide heating and be thermally regulated. The power and control connections links the wires for the heater power, the temperature sensors, security cut off systems in the cassette to a controller system such as a central PCB controller or any equivalent controlling system in the main unit. The connection can be automatically obtained as a result of the insertion of the cassette in the housing without any need for the operator to manipulate electrical wires or plugs. Due to the accurate guiding of the cassette along the slots of the housing, the plug-in connection of the cassette is aligned to the receiving connection in the rear of the housing along the guiding direction so as to confer rapid and reliable operational installation of the cassette in the housing.

The cassette also includes hinge means 187 mounted on the upper side of the cassette to allow the opening of the cassette in two halves for installing the food package. Closure of the cassette is carried out by latch means 188 located on the opposite side 184 of the cassette. The position of the hinge and latch means is not critical and many other variants for opening and closing the cassette can be envisioned for equivalent result. Also, the hinge means may be replaced by additional latches that would allow to separate the two half-trays.

Figure 7:
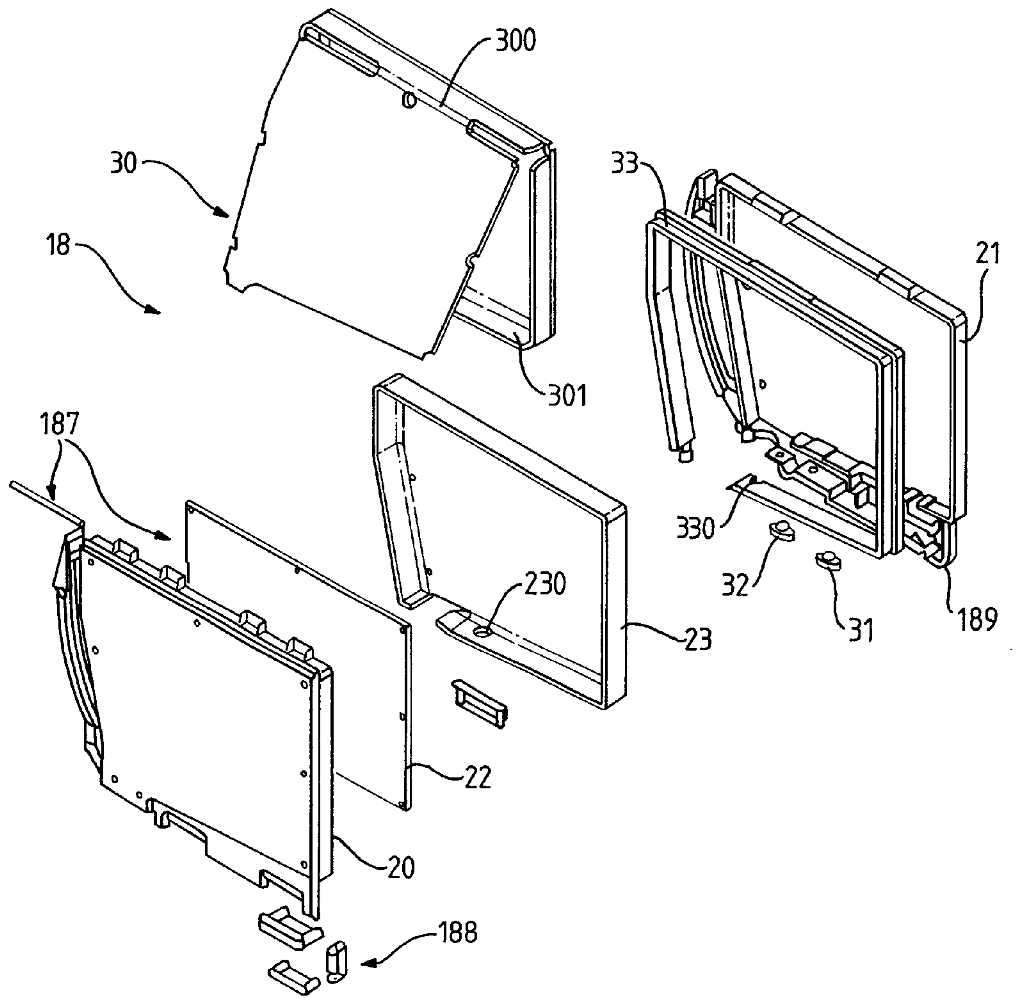
FIG. 7 is an exploded view of the cassette of FIG. 4.

FIG. 7 shows the detailed structure of the cassette according to a preferred embodiment. The external part of the cassette is formed from a rigid, heat insulated plastic covering assembly including a first and a second half trays 20, 21 assembled together along hinge means 187. The covering may be made in heat insulated plastic material such as polycarbonate. The thickness of the covering should be sufficient to provide both rigidity and proper insulation. Thickness for the covering of from ⅛ to ⅔ inch is preferred. The two half trays receive a flexible electrical resistive heater 30. The heater may preferably be formed of one single piece composed of six flaps forming a flexible box which opens along a bending line 300 at a position adjacent the hinge side of the cassette. Each flap of the heater takes position along one internal side of the plastic half trays 20, 21 so as to cover all the internal available surfaces of the trays for providing an efficient heating of the interior from different directions. The heater could also, as well, be formed of several discrete flaps connected together by suitable electrical wires or connections. The heater is mounted in sandwich between the half trays 20, 21 and heat conductive members such as a metal inner plate 22 and a metal inner tray 23 that form the contact surfaces with the food package. A peripheral gasket 33 positioned between the edges of the conductive members 22, 23 and the heater sides is further provided to ensure a protection of the heater in case of food leakage in the interior of the cassette. The gasket also enables to make the heater substantially water resistant so that the interior of the cassette can be wiped off with a sponge or be washed in a dishwasher. The structure of the cassette with thin film heater, although representing the best mode, could be replaced by any equivalent conduction based heating structure of sufficient and variable power density, electrically safe, easily cleanable and that can easily be formed in three dimensions to provide heat from different planes toward the interior of the cassette for quick but uniform heating of the food.

The cassette has further integrated temperature control means including at least two temperature sensors 31, 32 preferably located on the bottom side of the cassette. The bottom of the cassette is preferred for location of the sensors firstly because the product drains out toward the end of the pouch in this area and has contact with the sensor and secondly because the bottom has the lowest temperature. Sensor 31 is a product temperature sensor in an area that allows it to directly contact the food package. For that, the sensor is preferably mounted in an aperture 330 of the gasket 33 and an aperture 230 of conductive member 23 to be able to sense temperature at the surface of the food package. Sensor 32 is inserted between gasket 33 and heater internal side 301 to be able to sense the temperature of the heater. Preferably, sensor 32 is a boost sensor that is located in contact with the heater where the watt density is the highest. The sensors are electrically connected to the electrical plug-in connector 188 through suitable electrical wires protected in a small cavity 189 provided in the bottom of the half trays 20, 21. Preferably, a thermal cut off system may be installed in the cassette at the bottom, in contact with the heater where the watt density is the highest. In case of failure of the temperature monitoring system, the cut off system will allow to detect an abnormal heater temperature and to directly switch off the heater.

Figure 8:
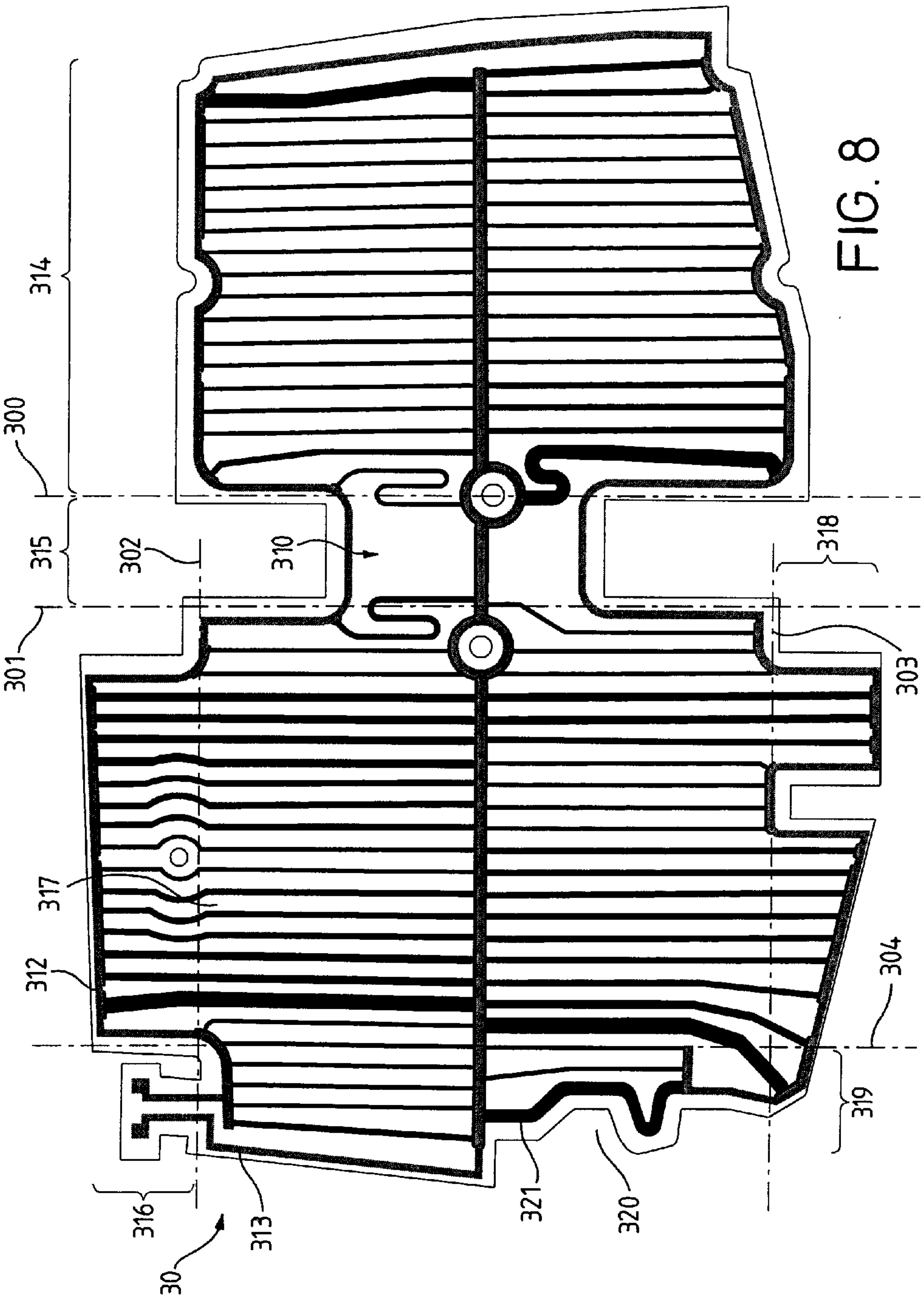
FIG. 8 is an evolute view of a preferred heater for the cassette.
Figure 9:
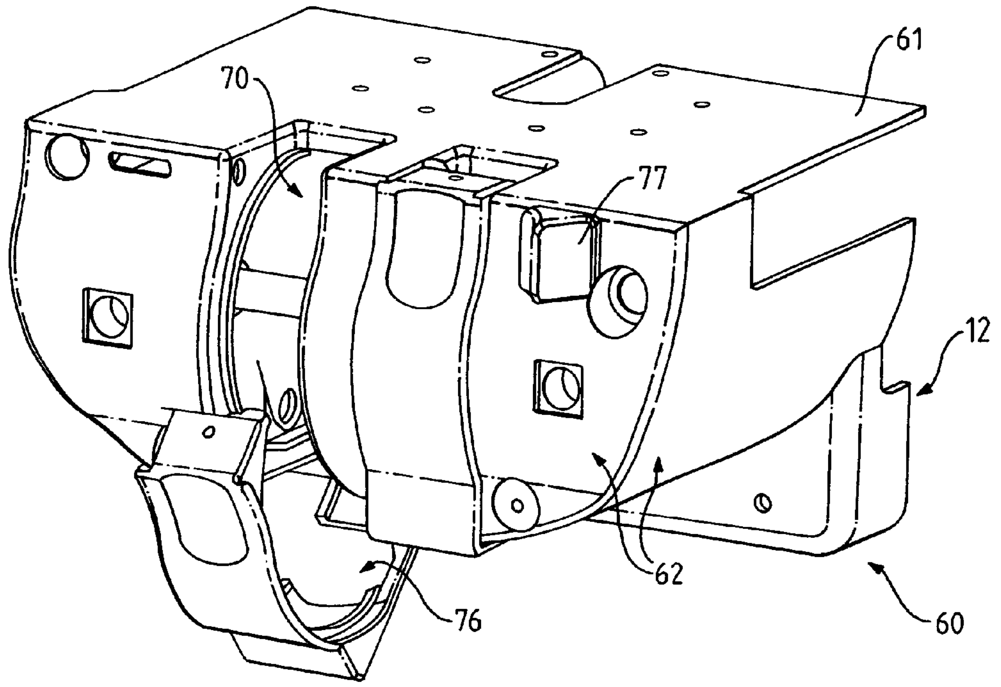
FIG. 9 is a partial view of the dispensing device showing the pumping assembly.

FIG. 8 illustrates an example of a suitable heater for the cassette. The heater is preferably a thin film heater that can be shaped in the form of a box member. A thin film element is constructed with a relatively large durable heating panel that provides a relatively low power density but efficient heating. The thin film element is employed here to heat the package in a relatively confined interior while reaching a contact temperature that should not go in excess of about 180° F., preferably at in a range of from 140 to 175° F. Due to the relative narrow spacing of the cassette and its heat insulation, the requirement for effective heating power to achieve that temperature is relatively low as compared to a normal electrical appliance such as an oven and the like. For example, a Cal rod-type resistance heater usually operates with rod heating element at a temperature about ten times higher than what is required (i.e., about 1000–1500° F.) and a power density that usually exceeds 10 W/sq.in. The use of Cad rod heaters would likely cause non-uniform heating patterns and overburning issues. In the present invention, it has been determined that the heater should provide an average watt density below 2 W/sq.in, even preferably below 1 W/sq.in but which confers an even heating of the food product. The benefit of thin film elements is that uniform heating throughout the food product can be obtained more easily by the ability offered to vary power density depending on the heating areas considered.

The thin film heater 30 used in the present invention, in a preferred mode, is initially formed as a flat flexible element. It has an electrically non-conductive surface 310, a thin film electrical conductor 311 deposited on the surface 310 and a pair of electrical terminals 312, 313 electrically coupled to the thin film electrical conductor. The non-conductive surface 310 may form the upper surface of a substrate comprising an electrically insulating polymeric layer. Electrically conductive film is electrically isolated by the polymeric layer. The polymeric layer may be a 4-mil polyester layer or any similar durable, heat and shock resistant plastic material. Electrically conductive material 311 most preferably is provided by a very thin film of conductive carbon-based ink or, alternatively, metal-oxide, for example, stannic oxide ($SnO_2$), nitrides, borides or carbides. The carbon-based ink may be deposited as a very thin film by printing on the plastic base. Then a clear adhesive plastic layer is layered on the printed surface to further protect the conductive track. The metal oxide film is most desirably deposited using a spray gun which atomizes and blows the metal oxide producing chemicals onto the polymer-based layer. Hence, the thin film becomes a molecularly bonded resistance film that is durable and can withstand repeatedly heating cycles without experiencing failures. Durability of such heaters is usually better than any other types of resistance heaters such those formed by adhering resistance heater wires to a substrate or when encircling a tubular substrate with a silicone blanket. Other solutions include chemical vapor deposition, which is a more expensive technology, silk screening, painting or other known techniques. Spaced-apart electrical terminals 312, 313 are preferably provided that connect the carbon based or metal oxide conductive track. A bus bar strip is provided along the periphery of the element and a second bus bar strip is provided along the center line of the element so as to distribute current substantially evenly all along the conductive layered surface. The bus bar terminals can be typically formed by silk screening techniques using, for example, silver or nickel-silver alloy, to form the bus bar. The thin film using a carbon ink conductive track printed on a polyester layer can be manufactured by Calorique, West Wareham, Mass.

As can be seen in FIG. 8, the thin film heating element is formed from a flat resistance evolute surface including resistance regions 314, 315, 316, 317, 318 and 319 corresponding to the six flaps of a resistance heating box that are intended to bend along bending lines 300, 301, 302, 303, and 304. In particular, the bottom surface of the heater corresponds to the resistance region 319 which includes the recess zone 320 for the passage of the discharge tube of the package. The recess zone 320 is demarcated by a conductive line 321 of higher power density, e.g., 0.65 W/sq.in, to maintain the base of the tube, e.g., the fitment of the tube connecting the package, at a sufficient elevated temperature range. It is readily apparent that the heating pattern can be modified easily depending upon the heating requirements by producing various conductive tracks in the different resistance regions. Almost all possibility is offered to heat the cassette in a very accurate manner. In particular, following Ohm's Law, areas of higher power density can be obtained by proportionally increasing the width of the conductive track. Conversely, when a lesser density is needed, the track can be made thinner.

Referring again to FIGS. 4 to 6, the cassette according to one important aspect of the invention has the ability to heat an amount of flowable food at or above 2 Kg, from ambient to a temperature above 140° F. in less than 2 and ½ hour, even preferably in less than 2 hour, even more preferably less than 1 and ½ hour. For that, the cassette has a reduced interior spacing "s", as demarcated by the two extensive heating surfaces 220, 230 which extend along the axial plane "P" of the cassette. The spacing "s" should be at lower than 2 inches, preferably lower than one and ¾ inches, even most preferably of from 1.0 to 1.75 inches. Remarkable results have been obtained by dimensioning the spacing "s" at 1.57 inches. Therefore, the capacity of the package is of little importance provided the spacing as defined is respected in the cassette. The heat-up time for the package can be achieved in less than an hour almost irrespective of the amount of product in the package. The reduced spacing also contributes to a more uniform heating of the package with absence of hot and cold spots in the product. In conjunction with the cassette's proportion requirement, it has also been determined that the average power density delivered by the heater should be at least 0.3 W/sq.in. and preferably from 0.3 W/sq.in to 0.8 W/sq.in., even more preferably from 0.45 to 0.65 W/sq.in. It has also been determined that the power density should preferably have zones of higher power density and zones of lower power density to adjust the heating pattern as a function of the location in the cassette. In particular, to compensate the natural tendency of hot air to move upward, the wattage density should preferably vary to provide more power in the bottom side of the heating surfaces of the cassette and less wattage density in the planar heating surfaces of the cassette. Therefore, the heater pattern ideally should provide a varying power density of from 0.45 to 0.65 W/sq.in with the higher values in the bottom parts and the lower values in the center parts of the cassette.

FIGS. 9 to 12 illustrate the pumping block 12 according to the invention. The block is of a compact size which makes it suitable for being mounted in a small footprint of the dispensing device thanks to a very unique pump configuration. The compact configuration of the pump block also contributes to improve its capacity to retain heat while avoiding heat loss. The block is also very easy to load with a discharge tube of the package and it can also be manipulated very safely without risks of being burned.

The peristaltic pump block comprises a housing 60 that is preferably formed of a top panel 61 and a front and lateral cover 62 in both of which are provided elongated vertical tube passages 63, 64. The tube passages are substantially aligned with one cassette location or set of slots as described earlier. The passage is positioned such that when a cassette is properly installed in operational position in a dispensing location, its axial plane is substantially aligned to the axial plane of the passage. The housing 60 can be made of materials or insulated with materials that conduct very badly heat so as to reduce the heat or frigorific losses outside the boundaries of the pump block.

Figure 10:
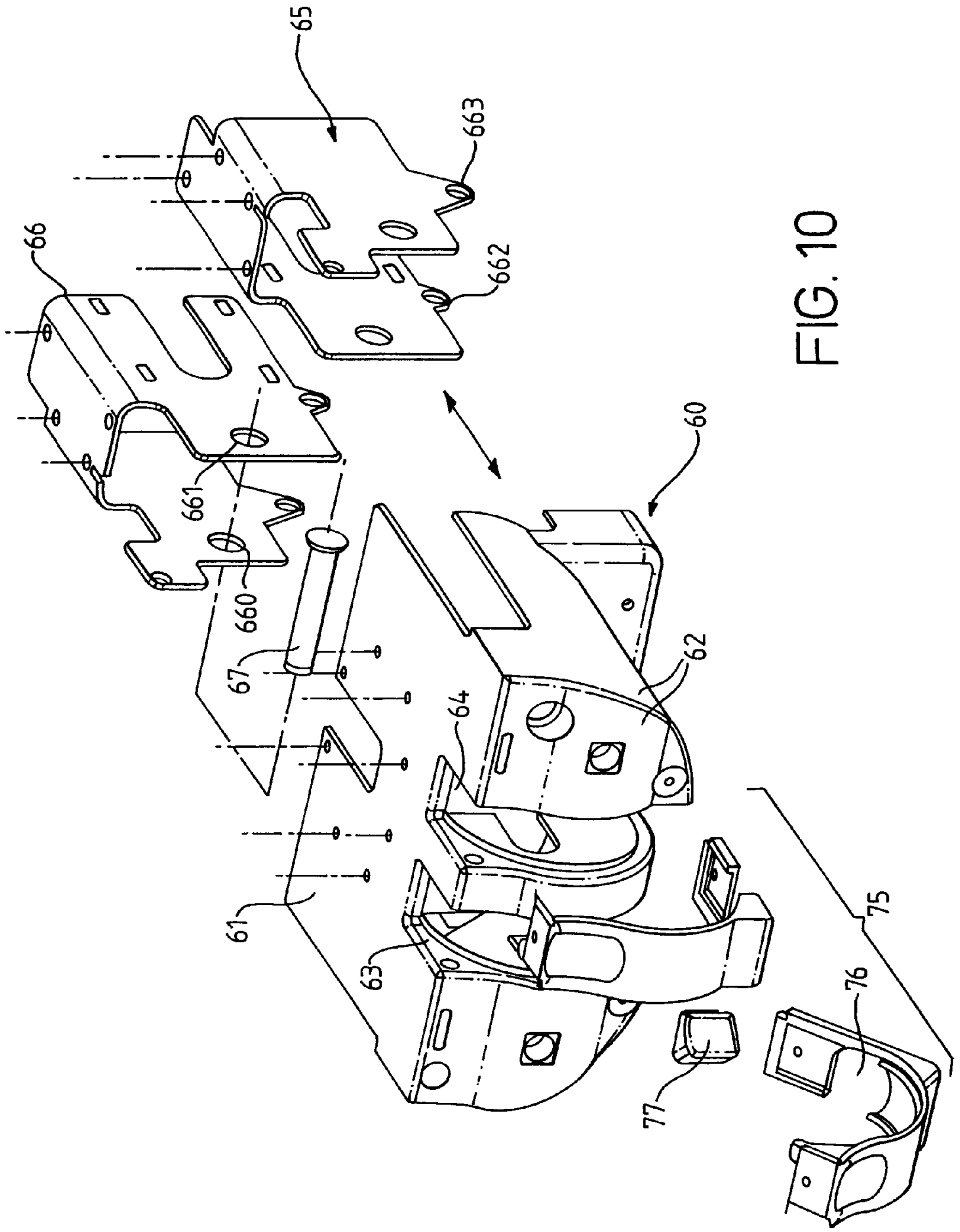
FIG. 10 is an exploded perspective view of the assembly of FIG. 9.

As is apparent in FIG. 10, the pump housing receives internally pump mounting frames 65, 66 having inverted U-shapes that laterally demarcate and close the passage 63, 64. Each frame 65, 66 serves for supporting and receiving a rotor assembly 70 that is mounted for rotation on axle 67 supported on bearings 660, 661 of the frame.

A stator assembly 75 is provided which has a substantially actuate shape to conform to the shape of the rotor assembly for a pinching effect on the discharge tube. The stator assembly is pivotally mounted on lower bearings 662, 663 of the frames 65, 66. The stator assembly is made thus moveable from an open position to a closed position. In the open position, the passages 63, 64 are cleared from above for an easy loading of the dispensing tube between the rotor assembly and the stator assembly. In the closed position, the passage is totally closed with no significant portion of tube visible from the exterior of the pump block. Therefore, the food product contained in the discharge tube can be maintained more easily at the required temperature while needing less energy for that. The stator assembly further comprises a lower outlet 76 for allowing the tube end to emerge from underneath the block. The stator assembly can be locked in a closed position by means of a locking mechanism that can manually be actuated by a latch lever 77. The latch lever 77 can move reciprocally to act on a latch member that fits a lateral hole of the rotor assembly.

Figure 11:
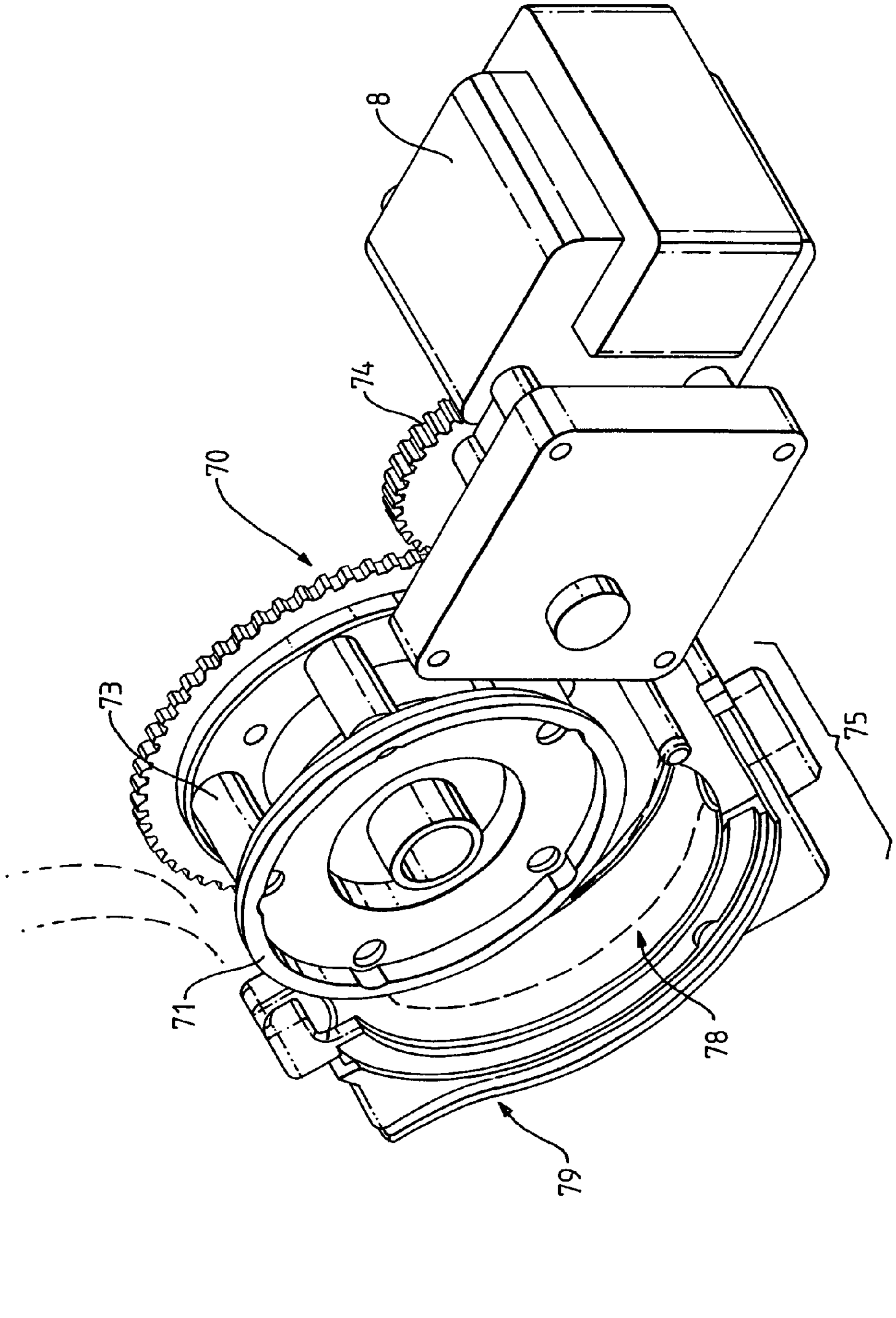
FIG. 11 is a perspective view of a preferred configuration of a peristaltic pump of the invention.
Figure 12:
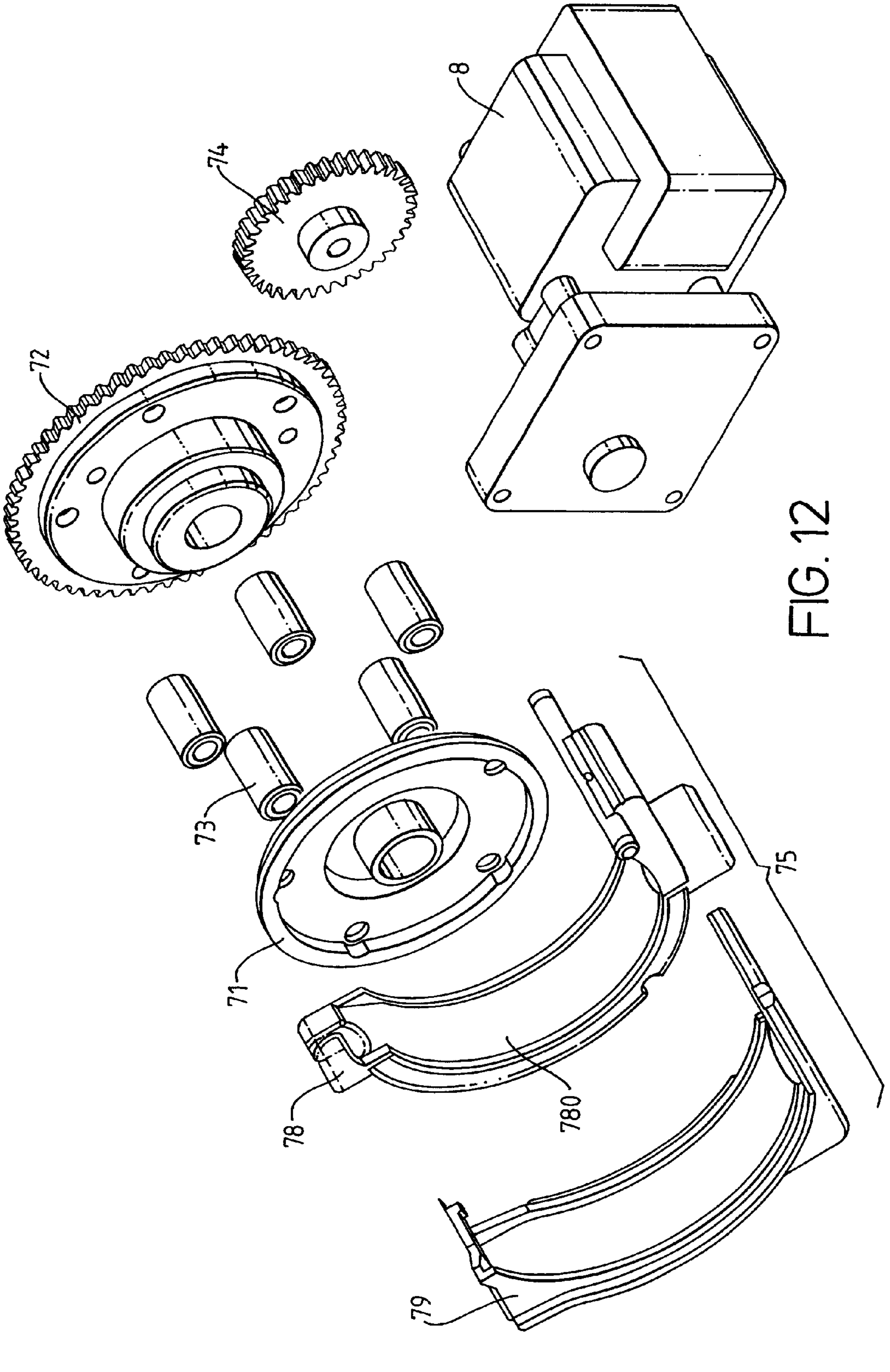
FIG. 12 is an exploded view of the pump of FIG. 12.

FIGS. 11 and 12 illustrate details of the rotor and stator assemblies as well as the motor and gear system. The stator is preferably made of an inner heat conductive stator member 78 and an outer heat insulated cover 79. The inner member 78 is inserted in the outer cover 79 and may be press fitted to the cover and/or attached by any suitable connection means. The discharge tube preferably receives direct heating from a cartridge heater lodged in the stator member (not shown). Hence, the discharge tube can be heated independently from the cassettes which thus provides several benefits. First, the temperature of the food in the discharge tube can be controlled more accurately and, for instance, at a lower temperature range than the temperature in the cassette so that the small amount of product in the tube suffers from a lower amount of heat and its quality is better maintained. Second, less energy is required to maintain the tube hot as only a portion of the pump that is directly in contact with the tube is heated. Third, control of the food temperature in the tube can be monitored and adjusted very accurately by having a temperature sensor or thermostat coupled to the stator member. Hence, a temperature feedback of the product in the tube can be obtained from the temperature sensor and sent to the controller that can decide on an action for the cartridge heater located in the stator member. In particular, when a cassette is plugged in a dispensing location, the controller receives a signal that commands in return the activation of the relevant cartridge heater of the pump assembly directly underneath the location. The cartridge heater heats up to and maintain a nominal temperature range of the tube, for instance, 150° F.+/−10° F. (this variable can be programmed in), whereas the stator thermistor provides the temperature feedback loop to the controller to maintain the temperature range. As a safety measure the stator member is equipped with a thermal cut off set, such as a solid state thermal cut off set, at a maximal temperature, for instance, 180° F. (this variable can be programmed in) to prevent the tube from overheating in the event of a failure or fault of the thermistor, controller or heater.

The rotor assembly is formed of two laterally spaced apart discs 71, 72 between which a series of pressing rollers 73 is mounted. The rollers are located at a radial distance of the stator internal surface 78 adapted for the compressing effect on the discharge tube that is necessary for transporting the flowable substance through the discharge tube. The disc 72 is a gear disc in connection with an electrical DC or stepped motor 8, optionally, via a secondary gear 74 of lower diameter for achieving the proper gear reduction.

The pump assemblies can deliver portion control of food upon a simple push on a corresponding button located on the front switch board. The presence of a cassette in the dispensing location will be detected by the controller. If the cassette is in place, the controller will run the pump on according to a portion duration stored in a nonvolatile memory of the controller. Upon initial setup, the operator may have the option to adjust the portion control by accessing a portion control button connecting to the PCB that can be placed in a remote location such as in the back of the dispensing unit. Visualization of the increase or decrease of the portion control may be realized by a series of LED's or by any suitable visualizing means.

Figure 13:
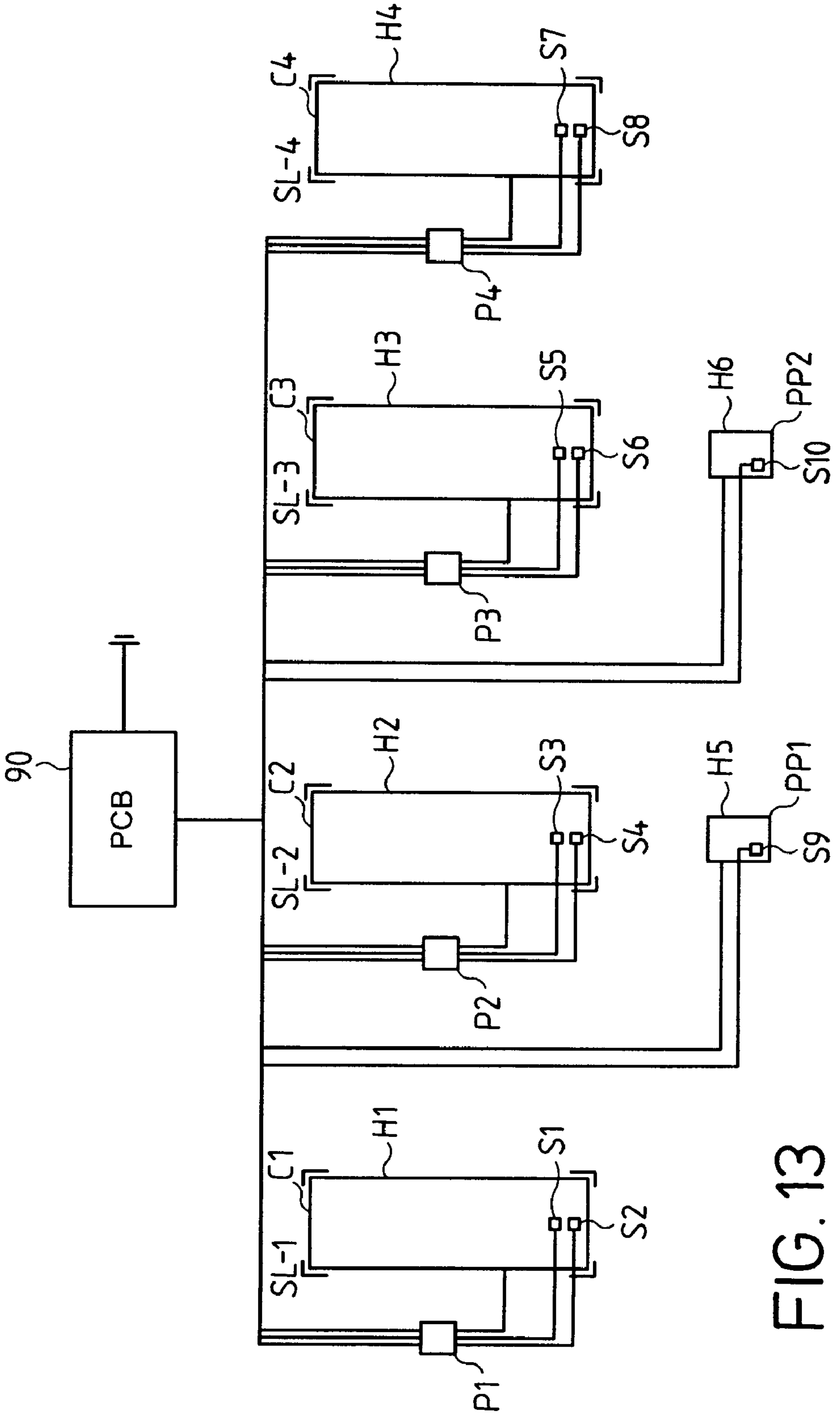
FIG. 13 is a block diagram of the dispensing device with cassettes of the invention.

Referring to the schematic block diagram for the thermal control of the device of the invention in FIG. 13, a series of cassettes C1 to C4 can be individually installed in a series of slot locations SL1 to SL4 by sliding engagement in the slot locations. Upon installation, the cassettes are automatically plugged in to a central PCB controller 90 through self-aligning plugging connections P1 to P4. As a result of the plugging of a cassette in a slot location, the corresponding product thermistor S1, S3, S5 or S7 in contact with the package starts sensing the product temperature and sends a signal to the PCB for activating the relevant heater H1 to H4 (via relays) to start heating the product. If the temperature sensed is found below a threshold value, e.g., 120° F., the PCB will enter a boost cycle and boost the heater under proportional power control and the heater thermistor S2, S4, S6 or S8 will control the heater temperature to a boost elevated set point, e.g., 175° F.+/− a tolerance value. As a result, if proportional control is chosen, the power sent to the heater will proportionally increase according to the differential between the product temperature to the new set point. Such a proportional power control has the benefit to favor a rapid heat-up of the food in the package while ensuring security with no risk of overshooting as the set point is progressively reached with a decreasing electrical power sent. The boost cycle will be maintained until the product thermistor reaches a product temperature set point corresponding to the desired product temperature at the bottom of the cassette, e.g., 150° F.+/− a tolerance value. Once the product in the bottom of the cassette has reached the set point, the product thermistor takes over the control, and the PCB will set a new heater set point, i.e., a monitoring set point, for the heater thermistor lower than the boost elevated set point. The temperature control is thus changed into a monitoring mode and the PCB will control the heater not to exceed the heater monitoring set point, e.g., 165° F. (variable). In the event, the package has been previously heated to a temperature higher than the threshold temperature initially sensed by the product thermistor, for example, if the product in the bottom of the cassette is between 121–140° F., the PCB will not activate the boost mode and will instead go to the maintenance mode, controlling the heater through the product thermistor.

The PCB controller also controls the on/off activation (via relays) of the heaters H5, H6 of the two pumps P2, P3 located in substantially vertical alignment with slot locations SL2 and SL3 that correspond to product dispensing locations. Thermistors S9, S10 are located inside the pump stators to provide feedback signals to the PCB to decide on an action for the heaters H5, H6.

Figure 14:
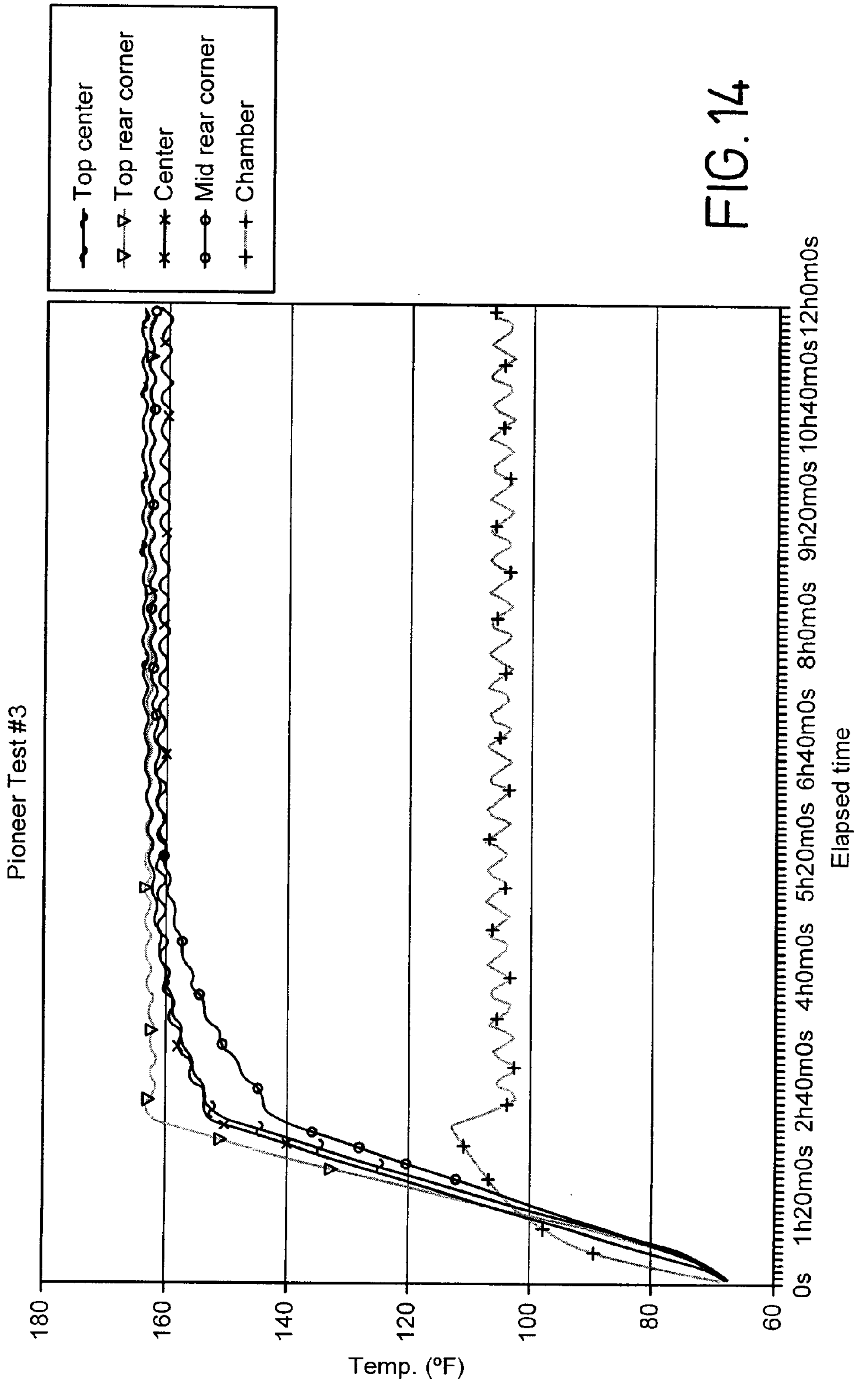
FIG. 14 is a graph showing the rapid heat-up curves of the dispensing device of the invention.

FIG. 14 shows the temperature rise in the dispensing unit of the invention in different locations with a interior spacing in the cassette "s" set at 1.57 inches. It appears clearly that the cassettes promote a rapid increase of the food product above 140° F. in about 2 hours or less. Furthermore, the inside chamber of the device remains at a relatively low temperature, i.e., at about 105° F., which denotes that the thermal losses are kept as minimal as possible and that the inside of the dispensing unit is safe for the operator with no risks of burns.

Where there is need for serving cold flowable food out of the dispensing unit, the device offers the possibility to accommodate cooling cassettes in at least one dispensing slot location of the device. The purpose of the cooling cassette is primarily to maintain the flowable product in a cold temperature range that is suitable for serving. The product does not necessarily require refrigeration but simply cooling slightly below ambient, i.e., 10 to 18° C., so that the freshness and shelf life of the product is prolonged. Furthermore, cooling of cassette ensures the product does not warm to a temperature that could be prejudicial to the quality or microbiological safety of the food product, especially if neighboring heating cassettes are provided in the dispensing unit.

Figure 15:
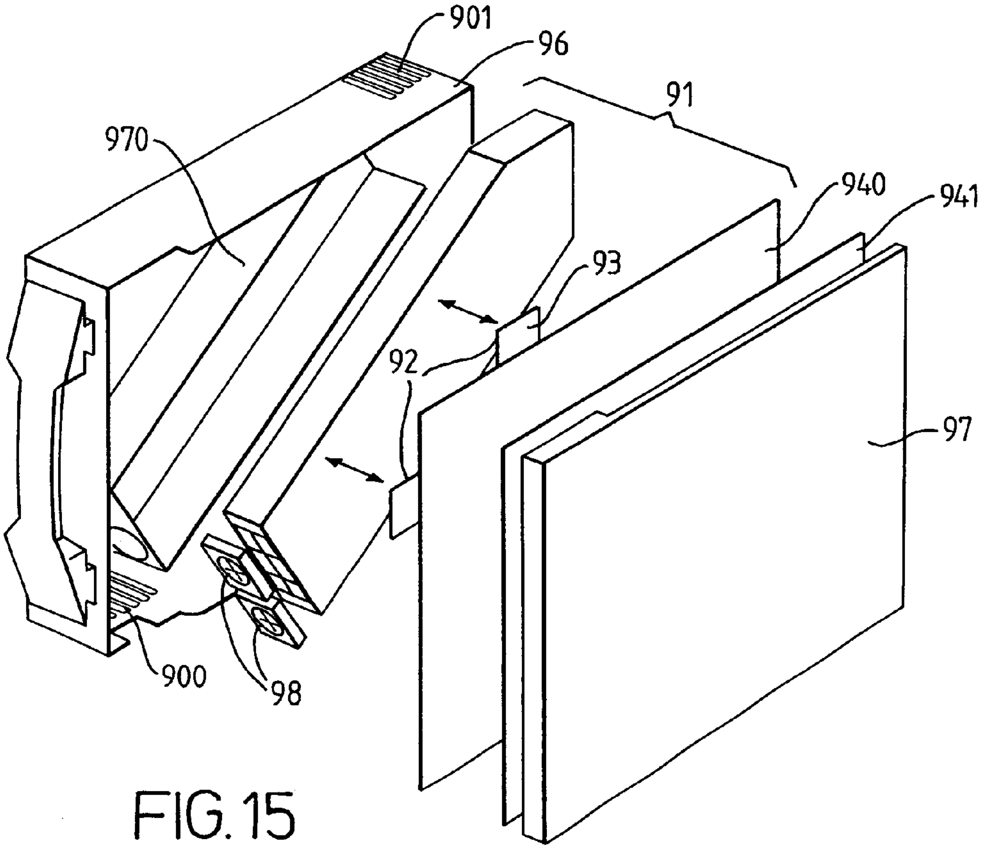
FIG. 15 is an exploded view of a cooling cassette according to one aspect of the invention.

FIG. 15 is an illustration of a preferred cooling cassette suitable for the device of the invention. The cassette include built-in cooling means 91 replacing the heater elements of the heating cassette. The general construction principle of the cassette remains identical as for a heating cassette of FIGS. 4 to 6 except for the cooling elements 91. The cooling elements comprises one and preferably at least two thermoelectric coolers (TEC) 92 with the cold side 93 of each cooler contacting a conductive plate 940 that forms an interior side of the cassette for contact with the food package (not shown) and the hot side of the cooler being mounted on the face of a heat exchanger 95. The other half-tray may have an insulation plate such as a polystyrene layer that further reduces the calorific loss outside of the cassette. The heat exchanger may further be coupled with at least one, preferably several fans 98, that promote heat dissipation. The cassette outer body may advantageously include two half-trays 96, 97 made in rigid plastic that are arranged to form together a closable assembly with suitable removable connection means. In the inside of one half-tray 96 can be provided means for fixing the cooling means such as an internal casing 970. Vents 900, 901 may further be provided in the half-tray to allow hot air to escape out of the cassette. The power capacity of each TEC is preferably of from 10 to 100 Watts, even preferably of from 20 to 60 Watts. The TEC are preferably supplied with full power without requirement for control thus making the device simple, reliable and low cost. The electrical low voltage power, typically 12 to 24V is supplied to the TEC from a power source located in the central unit via a suitable voltage converter. A central fan may be further provided within the housing of the dispensing unit with vents to outside to promote evacuation of the heat and moisture generated by the heat exchangers. Typically, when a cooling cassette is engaged in a slot connection, the logic senses the presence of a cooling cassette and the power to the pump heater is not activated. The fans is turned on by the PCB controller and power is sent to the TEC.

Figure 16:
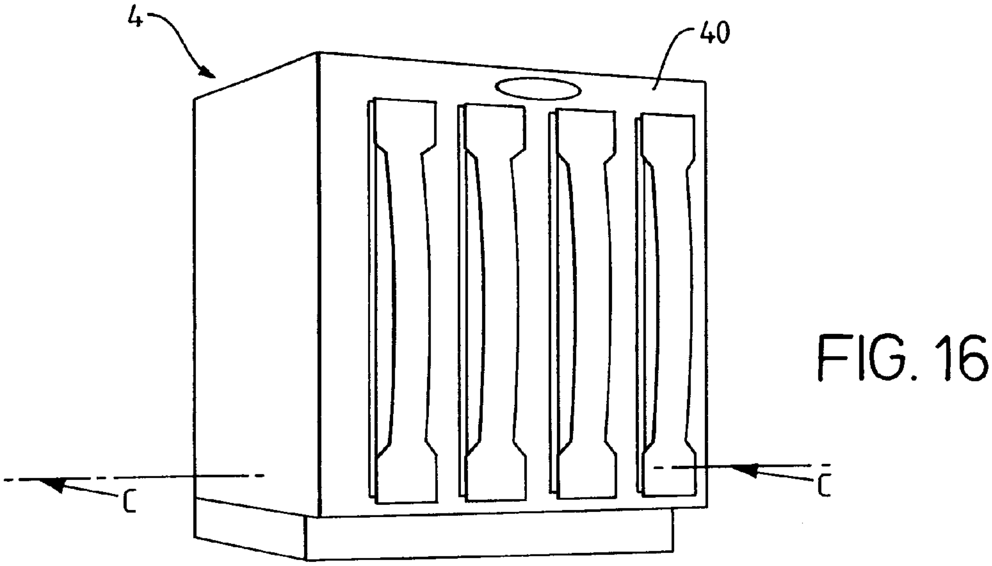
FIG. 16 represents a warming device of the invention that can accommodate a series of cassettes.
Figure 17:
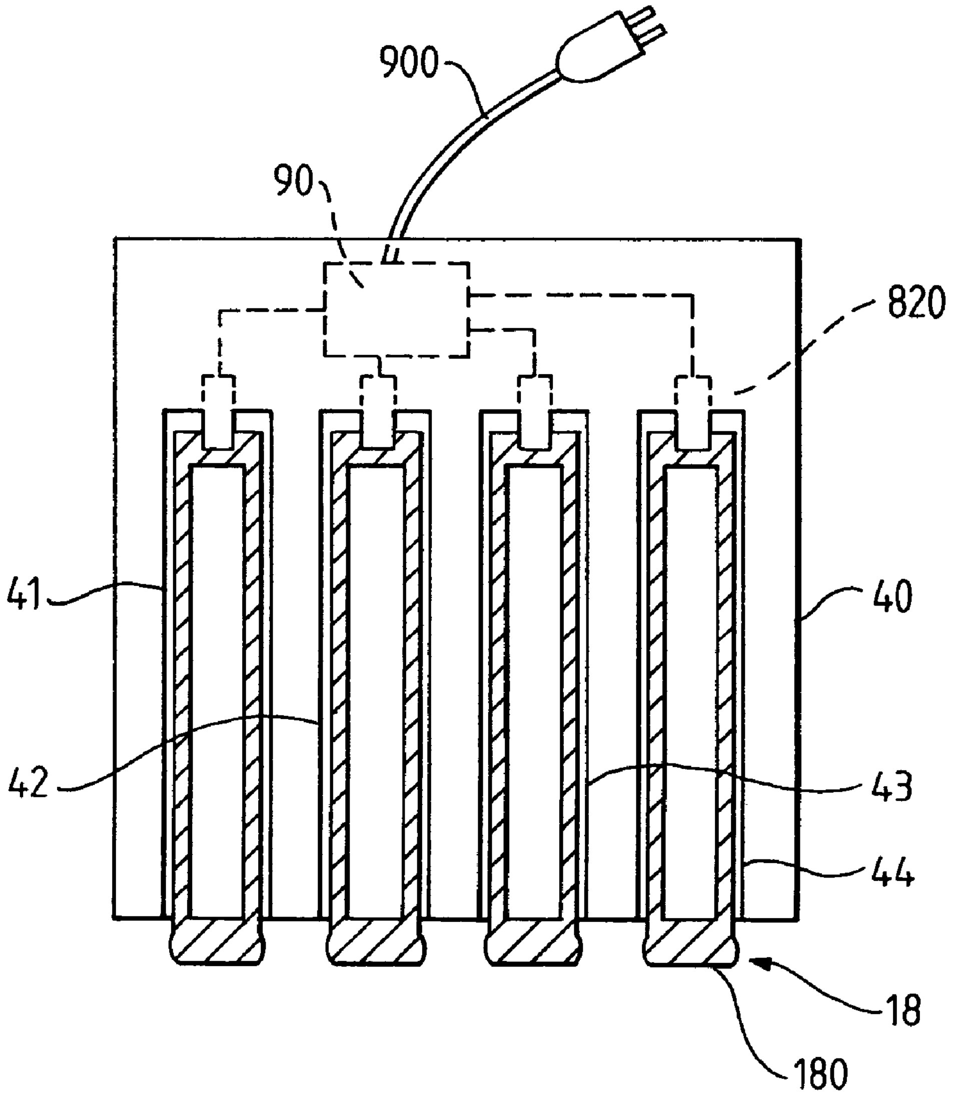
FIG. 17 is a cross-section view along line C—C of the warming device of FIG. 16.

FIGS. 16 and 17 represent an electrical warming device that can serve to provide electrical power to the heating cassette to put them into a heating mode but without dispensing means attached thereto. Such a device may be useful as an ancillary warming system in case the capacity of the dispensing device is proved to be not sufficient during peak hours or in certain circumstances or places, e.g., for service in football or baseball stadiums where the demand is highly concentrated in a very short period of time. The warming device 4, as illustrated, may be built on a principle very similar to the dispensing unit with a housing 40 comprising a series of elongated slot locations 41–43 which receive the closed heating cassettes 18 while leaving the handle part 180 of the cassettes externally apparent to ease handling of the cassette from outside by the operator. The housing may be insulated by suitable insulating materials such as plastic and/or polymeric foam. In the rear of the slot locations are provided electrical plug-in means 820 which allow quick electrical connection of the cassettes to the appliance. A central controller 90 may further be located in the housing in electrical connection with the electrical plug-in means 820 and in electrical connection with an electrical supply cord 900.

FIGS. 18, 19, 20 and 21 illustrate a preferred configuration of a pouch assembly adapted to be installed in the cassettes. The preferred pouch assembly is adapted to stand in a position that improves product evacuation and product heating efficiency while the pouch is still compatible for filling with the standard filling machines. However, the pouch assembly can fit both a cassette-type dispensers in which the pouch is loaded along a vertical plane and the known dispensers which receive the pouch laying flat along a sloped or horizontal plane. As result, it helps in lowering inventory costs and rationalizing management of product SKUs. For that, the pouch assembly 85 of the invention comprises a main pouch body 850 adapted to receive an amount of flowable food, a fitment member 851 sealingly attached to the pouch on a lower portion 852 of one side of the body, wherein the lower portion is capable of flexing at substantially 90 degrees with respect to the rest of the body to orient the fitment 851 downward when the pouch is supported in a standing position for product delivery and wherein there is provided a spacer means 860 at least partially engaging the fitment 851 to maintain a sufficient clearance inside the pouch to allow evacuation of the flowable product through the fitment.

Figure 19:
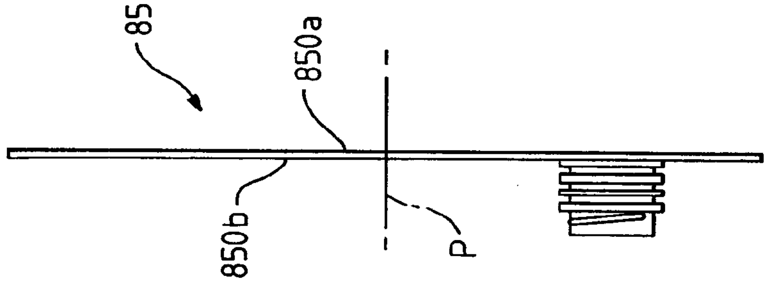
FIG. 19 is a transversal view of the pouch of FIG. 18.
Figure 18:
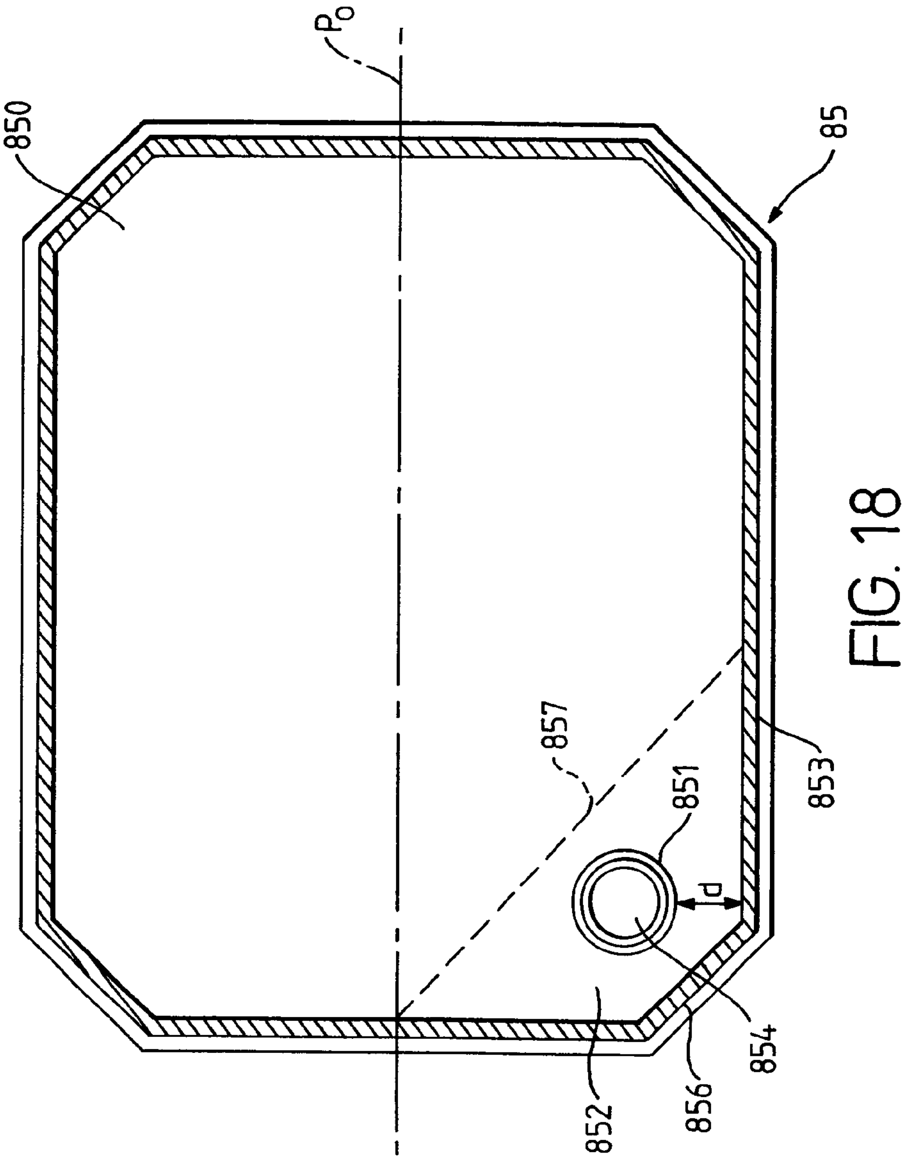
FIG. 18 is a side view of a pouch adapted to fit the cassettes according to a preferred embodiment.

FIGS. 18 and 19 illustrate the structure of the pouch and hose assembly according to a preferred embodiment of the invention. The disposable, substantially rectangular or polygonal, thin-walled pouch 85 is adapted to contain a flowable food product to be dispensed. The flexible pouch is made of plastic or another suitable film material that can withstand heat, i.e., temperature in excess of 140° F. The film may be of a material such as polyethylene, polyamide or PA/EVOH/PA laminate. The pouch preferably comprises two extensive sides 850*a*, 850*b* sealed together along a peripheral sealed edge 853. Secured to the bottom corner region 852 of the pouch's side 850*b* is the fitment 851 that defines an outlet 854 for dispensing the food product.

In a preferred embodiment, the bottom corner region has a truncated corner 856 to reduce the dead zone that is submitted to folding when the pouch is put into place in the cassette as it will be apparent in the next figures. Preferably, the fitment is located in region at a distance "d" from the sealed edge 853 of the pouch that is sufficient to provide a proper folding of the corner region 852 along a line 857 that is inclined with respect to the median longitudinal plane $P_0$ of the pouch. If this distance "d" is too long, the portion submitted to folding may be too large which would cause problems to evacuate product from dead zones of the folded portion. If the distance is too short, the portion may have difficulties to fold properly and it may be difficult to engage the fitment through the passage. Furthermore, if the distance between the two plies 850*a*, 850*b* of the pouch is too short due to the proximity of the corner, it could cause a problem to engage the spacer with risks of accidentally puncturing the pouch. Depending on the pouch and fitment's sizes, the distance from the edge may vary greatly. However, it should approximately be between 1 to 3 inches to accommodate a standard pouch capacity.

Figure 20:
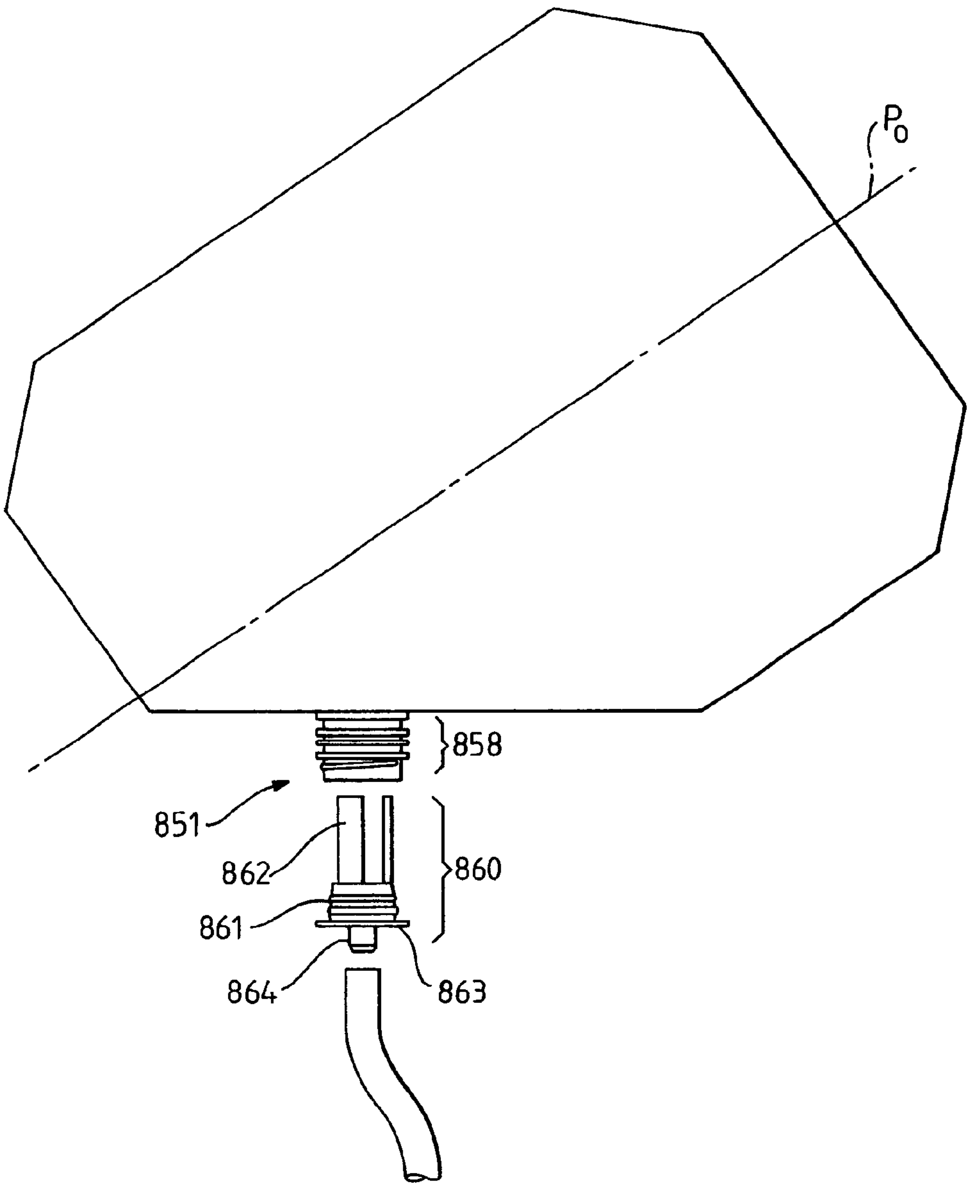
FIG. 20 is a side view of a pouch assembly adapted to fit the dispensing system of the invention.

As best shown in FIG. 20, the fitment has usually an external thread or snap ring 858 for engagement with a cap (not shown) that tightly closes the pouch after filling with the food product for transportation and storage before the pouch is for the first time inserted in the dispensing device.

Figure 21:
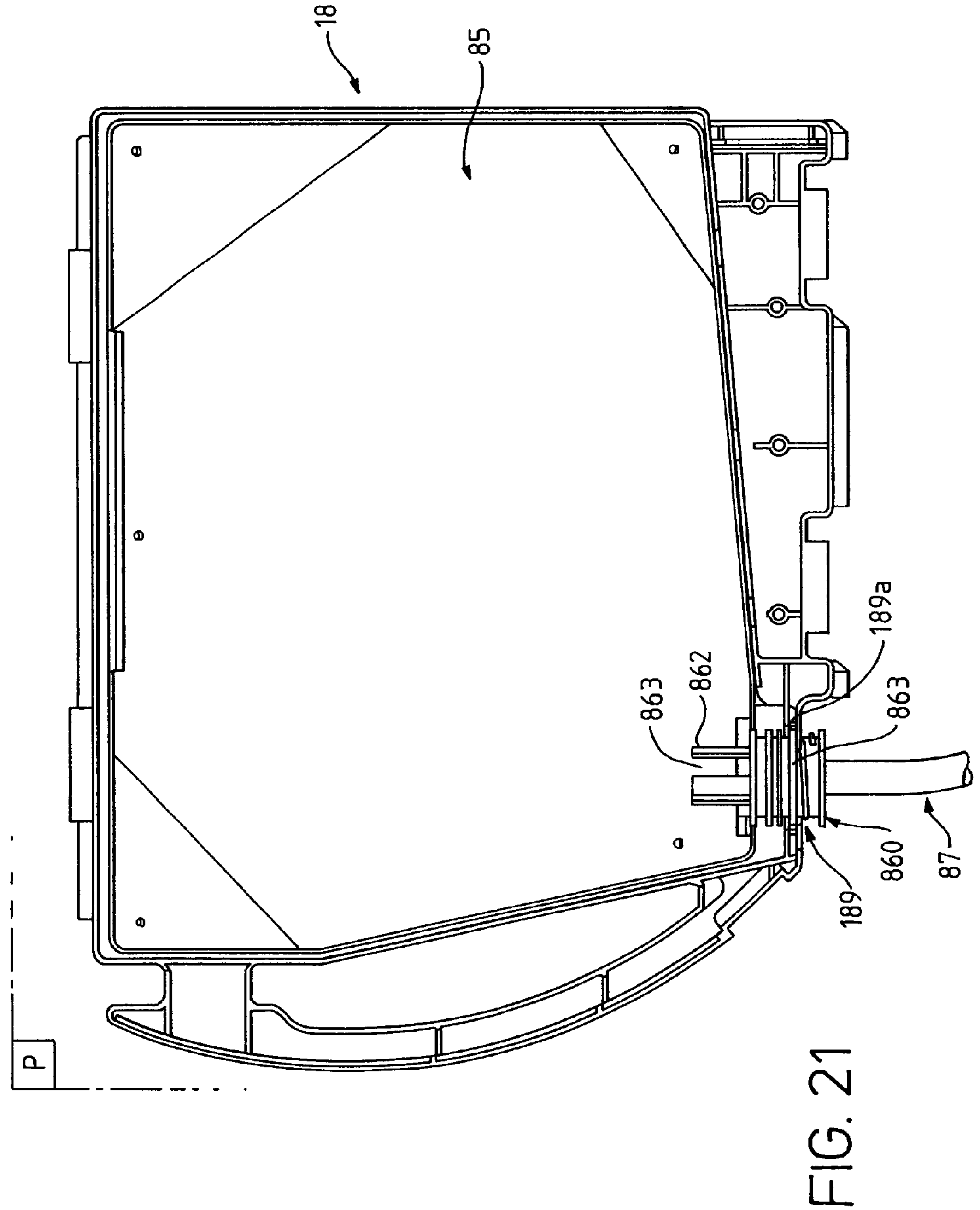
FIG. 21 is a cross sectional view of the cassette and pouch assembly fitting the cassette.

As best shown in FIG. 21, the pouch assembly is inserted into the cassette assembly 18 of a structure as earlier described. The passage 189 of the cassette for enabling the fitment 851 to stand therethrough at substantially the lowest point of the cassette when the cassette is maintained in the vertical standing position. The bottom side supporting the pouch body may further present a sloped profile to increase the evacuation in direction of the passage.

As a consequence of its insertion within the interior of the cassette, the body 850 of the pouch aligns itself along the axial plane P of the cassette whereas the corner region 852 that supports the fitment is folded substantially at 90 degrees with respect to the rest of the body along line 857 so that the fitment can properly orient itself downward through the intended passage. As a result, the outlet of the fitment is put in a position that is the lowest of the pouch thereby improving the evacuation of the food in the cassette. At the same time, the body of the pouch has its two main sides intimately contacting the larger heating surfaces of the cassette thereby rendering the heat transfer particularly effective.

According to the invention, a spacer means is provided under the form an adapter 860 that fits into the fitment 851 via a thread 861 and has a central aperture able to establish fluid connection with the outlet 854 of the fitment. The spacer means has the function to maintain a sufficient clearance in the vicinity of the outlet inside the pouch where there is a risk for the pouch to collapse due to the folding of the corner portion 852. For that, the spacer means preferably axially engages the fitment and has at least one internally protruding rigid element that extends beyond the outlet inside the pouch. Even more preferably, there are a plurality of prongs 862 extending axially and internally on the periphery of the aperture. The prongs configuration forms a sufficient clearance around the aperture while providing radial passages 863 of sufficient surface for not disturbing the flow of product from the interior of the pouch through the fitment assembly. The prongs keeps the back side of the pouch from choking of the flow of product from the pouch. They proved to be essential to the vertical configuration in the cassette and desirable for the horizontal or inclined flat configuration in traditional dispensing systems. As shown in FIG. 21, the adapter may comprise a transversally raising part 863 that fits in a slot 189*a* of the cassette to secure the fitment assembly into place.

The pouch assembly further includes a discharge tube 87 that can engage the volumetric displacement pump of the dispensing unit. The discharge tube 87 is connected to the pouch assembly by press fitting on a gland 864 of the adapter located at the terminal or lower end of the adapter.

The pouch assembly embraces many variants that may be found equivalent to the preferred embodiment apparent in the figures. For instance, the spacer means could be made integral to the fitment instead of being supported by the adapter. The fitment could thus protrude internally by prongs or any equivalent internally protruding elements. Another possible variant can consists in making the spacer means under the form of an apertured tubular member replacing the discontinuous spaced apart prongs. Another variant can consists in making the spacer means as a central rod attached to the outlet or aperture by radial ribs or a grid.

The benefit of having a fitment sealingly attached to a corner portion of the bag but still on one side of the pouch is that the pouch assembly of the invention can use the technology of the FDA approved preformed bags and be aseptically filled in standard filling machines. Preformed bags are commonly used in the food industry. Contrary to from-fill-seal bags, the preformed bags are produced with a capped fitment, sterilized and sent empty to a filling station either as separate bags or a chain of bags connected via a continuous web. Therefore, the pouch of the invention may be produced from preformed bags that have a food capacity of from 3 to 10 liters, as approved by the U.S. Food and Drug Administration.

The pouch may alternatively employ the form-fill-seal technology which consists in aseptically filling the bag from an upper edge that is subsequently sealed right after filling. In that event, the fitment would previously be sealed on the corner region as aforementioned. The outlet would have to be made by puncturing the pouch side inside the fitment to establish fluid connection. Puncturing may be carried out before engaging the adapter by using any suitable piercing element or by means of the adapter itself that pierces the pouch when securely engaging the fitment.

The terms "vertical" or "standing" in the present invention refer to a position or configuration strictly vertical or close to vertical so that flow of product by gravity is promoted. In particular, a pouch standing at an acute angle to vertical would still be considered as part of the present invention.

Further details regarding the pouch assembly can be found in a co-pending U.S. patent application Ser. No. 10/032,169, filed Dec. 21, 2001 by Balakrishna Reddy and Richard Artman entitled "Food Pouch for Dispensing a Flowable Food Product From a Cassette-type Dispenser" (W+S Ref. 88265-7217), the content of which is expressly incorporated herein by reference.

While various description of the present invention are described above, it should be understood that the various features can be used singly or in any combination thereof. Therefore, the invention is not to be limited to only specifically preferred embodiments depicted herein. For instance, it is possible to use the dispensing device only for maintaining food product in their package in a cool state. Hence, cassettes in the dispensing unit might be only cooling cassettes. Furthermore, it can also be envisioned to refrigerate food products in the cassettes, i.e., at temperature slightly higher than 32° F., by providing more powerful refrigerating means for example to dispense milk-based flowable food such as acidified milk, liquid cheese or yogurt and the like.

What is claimed is:

1. A dispensing device for dispensing flowable food product comprising:

a housing; and at least one removable cassette within the housing adapted for receiving a package containing flowable food, wherein the cassette has a substantially closed interior for receiving the package and comprises built-in temperature exchanger providing direct heat or cooling to the interior of the cassette generally along a major side of the cassette and a heat insulator to provide insulation against radiant or frigorific loss to outside the interior of the cassette.

2. A dispensing device according to claim 1, wherein at least two extensive conduction heating surfaces extending substantially parallel to the axial plane are provided in the cassette, and the interior of the cassette has a built-in heater for providing direct heat to the surfaces, wherein the conductive heating surfaces are spaced by less than 2 inches.

3. A dispensing device according to claim 2, wherein at least five extensive conduction heating surfaces extending generally parallel or perpendicular to the major side are provided, and the built-in heater is configured for providing direct heat to the at least five surfaces.

4. A dispensing claim device according to claim 3, wherein the conduction heating surfaces provide an average power density of at least 0.3 W/sq.in.

5. A dispensing device according to claim 3, wherein the conduction heating surfaces provide an average power density of less than 1 W/sq.in.

6. A dispensing device according to claim 5, wherein the cassette has a top side and a bottom side, the conduction heating surfaces provide a watt density that varies as a function of location on the heating surfaces and is between 0.3 to 0.8 W/sq.in. and wherein higher watt densities are distributed on the bottom side of the cassette.

7. A dispensing device according to claim 1, wherein the conduction heating surfaces are heated by a flexible heater folded along at least two distinct planes.

8. A dispensing device according to claim 7, wherein the heater is at least one thin film heater.

9. A dispensing device according to claim 7, wherein the heater is box-shaped.

10. A dispensing device according to claim 1, wherein the cassette is made of two half trays.

11. A dispensing device according to claim 1, wherein the cassette includes at least one guiding edge to fit a complementary guiding receiving portion of the housing and self-aligning plug-in electrical connection adapted to fit complementary electrical receiving portion, wherein the electrical plug-in connection is arranged to plug in the electrical receiving means as resulting from the complementary fitting of the cassette within the housing.

12. A dispensing device according to claim 1, wherein there is at least a pair of cassettes with the cassettes being interchangeable in the housing.

13. A dispensing device according to claim 1, wherein at least a cassette is arranged in a standing location where the package in the cassette is capable of being operatively connected to a valve means to be operable in a dispensing mode.

14. A dispensing device according to claim 13, wherein the valve means is a peristaltic pump capable of engaging a discharge tube of the package.

15. A dispensing device according to claim 14, wherein the peristaltic pump is oriented so that its rotor plane for the passage of the discharge tube is substantially aligned with the major side of the cassette.

16. A dispensing device according to claim 15, further comprising a heater configured for heating the discharge tube in the peristaltic pump.

17. A dispensing device according to claim 16, wherein heater is configured to heat the discharge tube at a temperature lower than the product in the cassette.

18. A dispensing device according to claim 1, wherein each cassette is controlled by a proportional controller having a control circuit and sensor signal that regulates the electric power based on the signal that is proportional to the differential of sensor temperature from the set point.

19. A dispensing device according to claim 1, wherein each cassette can be controlled in a boost heating mode during warm-up of the package and a monitoring heating mode once the package has substantially reached a monitoring temperature point.

20. A dispensing device according to claim 19, wherein both boosting and monitoring modes are performed by the use of a single resistance circuit.

21. A dispensing device according to claim 19, wherein the temperature in the cassette is controlled by both a temperature sensor in contact with the heater and a temperature sensor in contact with the package within the cassette.

22. A dispensing device according to claim 21, wherein the heater temperature sensor helps to set an elevated set point during the boost heating mode and a monitoring set point during the monitoring heating mode lower than the elevated set point while the product temperature sensor helps to set the product temperature range.

23. A dispensing device according to claim 1, wherein the thermal exchanger comprises a cooling device that includes at least one TEC delivering a power of at least 20 Watts.

24. A food heating device comprising a plurality of removable cassettes adapted for providing a high capacity in heated flowable food whereby the removable cassettes receive packages containing food; each cassette having an interior that and contains internal direct conduction heating surfaces wherein the interior of the cassette has a width of less than 2 inches, and having an insulator adapted to reduce radiant heat loss and facilitate handling and loading of the cassette out of and into the heating device.

25. A heating device according to claim 24, wherein the interior of the cassette has a width of less than one and ¾ inches.

26. A heating device according to claim 24, further comprising peristaltic pumps adapted to engage a discharge tube of the food pouch that have a rotor plane oriented in generally alignment with a major side of the cassettes when in place in dispensing location.

27. A heating device according to claim 24, further comprising slot locations for receiving the cassettes in predetermined power supply positions and electrical and control connections adapted to plug-in with the cassettes as resulting from the engagement of the cassettes in the predetermined power supply position.

28. A food heating device comprising a plurality of removable cassettes adapted for providing a high capacity in heated flowable food whereby the removable cassettes receive packages containing food; each cassette having an interior that contains internal direct conduction heating surfaces; wherein the interior of the cassette has a width of less than 2 inches, and each cassette comprises an insulator adapted to reduce radiant heat loss and facilitate handling and loading of the cassette out of and into the cassette; the device being configured for reception in and dispensing by a dispensing device.

29. A heating device of small footprint adapted for providing a high throughput of heated flowable food whereby at least a pair of closed cassettes having a major axial plane is provided for individually receiving a food-containing package; the cassettes comprising a heated interior spacing of less than 2 inches and wherein it comprises at least one peristaltic pump having a rotor with a rotor diameter oriented substantially parallel to the major axial plane of at least one of the cassette.

30. A heating device according to claim 29, wherein the device has at least four locations for receiving the cassettes and has an external width of less than about 10 inches.

31. A dispensing device adapted for providing a heated flowable food wherein, at least one removable cassette is provided for individually receiving a food-containing package wherein the cassette is effective to heat the food package of at least 2 Kg, from ambient to a product temperature above 140° F., in less than 2 and ½ hour, wherein the cassette comprises at least one conduction heating surface extending substantially parallel to its axial plane and comprises an insulator to provide thermal insulation to the interior of the cassette.

32. A cassette for heating or cooling a flowable food product, the cassette having a substantially closed interior for receiving a package of a flowable food product and comprising built-in temperature exchange means providing direct heat or cooling to at least one extensive heat conduction surface extending substantially parallel the axial plane of the cassette; and heat insulating means that substantially reduces radiant or frigorific loss to outside the interior of the cassette.

33. A method for rapidly and uniformly heating a food package in a dispensing unit which comprises the use of at least one removable cassette provided for individually receiving a food-containing package wherein the cassette is effective to heat a food package while delivering an average power density of at least 0.3 W/sq. in. but less than 1 W/sq.in. by direct conduction effect with heating elements directing heat at least in a direction transverse to the axial plane of the cassette through the width of the cassette.

34. A method according to claim 33, wherein the cassette is maintained in a standing position along its axial plane to promote downward flow of product by gravity.

* * * * *

UNITED STATES PATENT AND TRADEMARK OFFICE

CERTIFICATE OF CORRECTION

PATENT NO. : 6,871,015 B2
DATED : March 22, 2005
INVENTOR(S) : Gutierrez et al.

It is certified that error appears in the above-identified patent and that said Letters Patent is hereby corrected as shown below:

<u>Column 21</u>,
Line 23, change "cassette" to -- cassettes --.

Signed and Sealed this

Twenty-first Day of June, 2005

JON W. DUDAS
*Director of the United States Patent and Trademark Office*